(12) United States Patent
Feezor et al.

(10) Patent No.: US 11,554,027 B2
(45) Date of Patent: Jan. 17, 2023

(54) SYSTEMS AND METHODS FOR NASAL SUPPORT

(71) Applicant: Siesta Medical, Inc., Los Gatos, CA (US)

(72) Inventors: Christopher Feezor, San Jose, CA (US); Erik van der Burg, Los Gatos, CA (US); Peter Martin, Mountain View, CA (US)

(73) Assignee: Siesta Medical, Inc., Los Gatos, CA (US)

(*) Notice: Subject to any disclaimer, the term of this patent is extended or adjusted under 35 U.S.C. 154(b) by 168 days.

(21) Appl. No.: 16/565,936

(22) Filed: Sep. 10, 2019

(65) Prior Publication Data

US 2020/0078194 A1    Mar. 12, 2020

Related U.S. Application Data

(60) Provisional application No. 62/729,032, filed on Sep. 10, 2018.

(51) Int. Cl.
| | |
|---|---|
| *A61F 2/46* | (2006.01) |
| *A61F 2/18* | (2006.01) |
| *A61F 2/00* | (2006.01) |
| *A61F 2/30* | (2006.01) |

(52) U.S. Cl.
CPC ......... *A61F 2/4618* (2013.01); *A61F 2/0077* (2013.01); *A61F 2/186* (2013.01); *A61F 2002/0086* (2013.01); *A61F 2002/30761* (2013.01)

(58) Field of Classification Search
CPC combination set(s) only.
See application file for complete search history.

(56) References Cited

U.S. PATENT DOCUMENTS

| | | | |
|---|---|---|---|
| 5,192,303 | A | 3/1993 | Gatturna et al. |
| 5,988,171 | A | 11/1999 | Sohn |
| 6,161,541 | A | 12/2000 | Woodson |
| 6,482,178 | B1 | 11/2002 | Andrews et al. |
| 7,780,730 | B2 | 8/2010 | Saidi |
| 8,133,276 | B2 | 3/2012 | Saidi |
| 8,784,488 | B2 | 7/2014 | Saidi |
| 9,480,594 | B2 | 11/2016 | Saidi et al. |
| 9,597,220 | B2 | 3/2017 | Gonzales et al. |
| 2003/0149447 | A1* | 8/2003 | Morency .......... A61B 17/06166 606/228 |
| 2005/0092332 | A1 | 5/2005 | Conrad et al. |
| 2005/0126563 | A1 | 6/2005 | van der Burg et al. |
| 2006/0070626 | A1 | 4/2006 | Frazier et al. |
| 2006/0150986 | A1 | 7/2006 | Roue et al. |
| 2006/0201519 | A1 | 9/2006 | Frazier et al. |
| 2006/0207606 | A1 | 9/2006 | Roue et al. |

(Continued)

*Primary Examiner* — Yashita Sharma
(74) *Attorney, Agent, or Firm* — Knobbe, Martens, Olson & Bear, LLP

(57) ABSTRACT

Cartilage support implants for nasal valve support and delivery systems are described. The cartilage support implant can include one or more elongate bodies comprising one or more anchors. The cartilage support implant can be designed to be a permanent implant extending along the midline of a patient's nose, from the nasal bone to the lower lateral cartilage. Methods of placing the cartilage support implant and retrieving the cartilage support implant are also described.

25 Claims, 21 Drawing Sheets

(56) References Cited

U.S. PATENT DOCUMENTS

| | | |
|---|---|---|
| 2006/0207607 A1 | 9/2006 | Hiratsuka et al. |
| 2006/0207608 A1 | 9/2006 | Hiratsuka et al. |
| 2006/0207612 A1 | 9/2006 | Jackson et al. |
| 2007/0119463 A1 | 5/2007 | Nelson et al. |
| 2007/0144539 A1 | 6/2007 | van der Burg et al. |
| 2008/0023012 A1 | 1/2008 | Dineen et al. |
| 2008/0027480 A1* | 1/2008 | van der Burg ..... A61B 17/0469 606/199 |
| 2008/0027560 A1 | 1/2008 | Jackson et al. |
| 2008/0035160 A1 | 2/2008 | Woodson et al. |
| 2008/0053461 A1 | 3/2008 | Hiratsuka et al. |
| 2008/0058584 A1 | 3/2008 | Hiratsuka et al. |
| 2008/0066769 A1 | 3/2008 | Dineen et al. |
| 2008/0208265 A1 | 8/2008 | Frazier et al. |
| 2009/0312791 A1* | 12/2009 | Lindh, Sr. ........ A61B 17/06166 606/228 |
| 2010/0280611 A1 | 11/2010 | Saidi |
| 2014/0243975 A1* | 8/2014 | Saidi ...................... A61F 2/186 623/10 |
| 2015/0012090 A1 | 1/2015 | Saidi |
| 2016/0058556 A1 | 3/2016 | Rosenthal et al. |
| 2017/0079774 A1 | 3/2017 | Saidi et al. |
| 2017/0105836 A1 | 4/2017 | Baron et al. |
| 2017/0143532 A1 | 5/2017 | Gonzales et al. |

\* cited by examiner

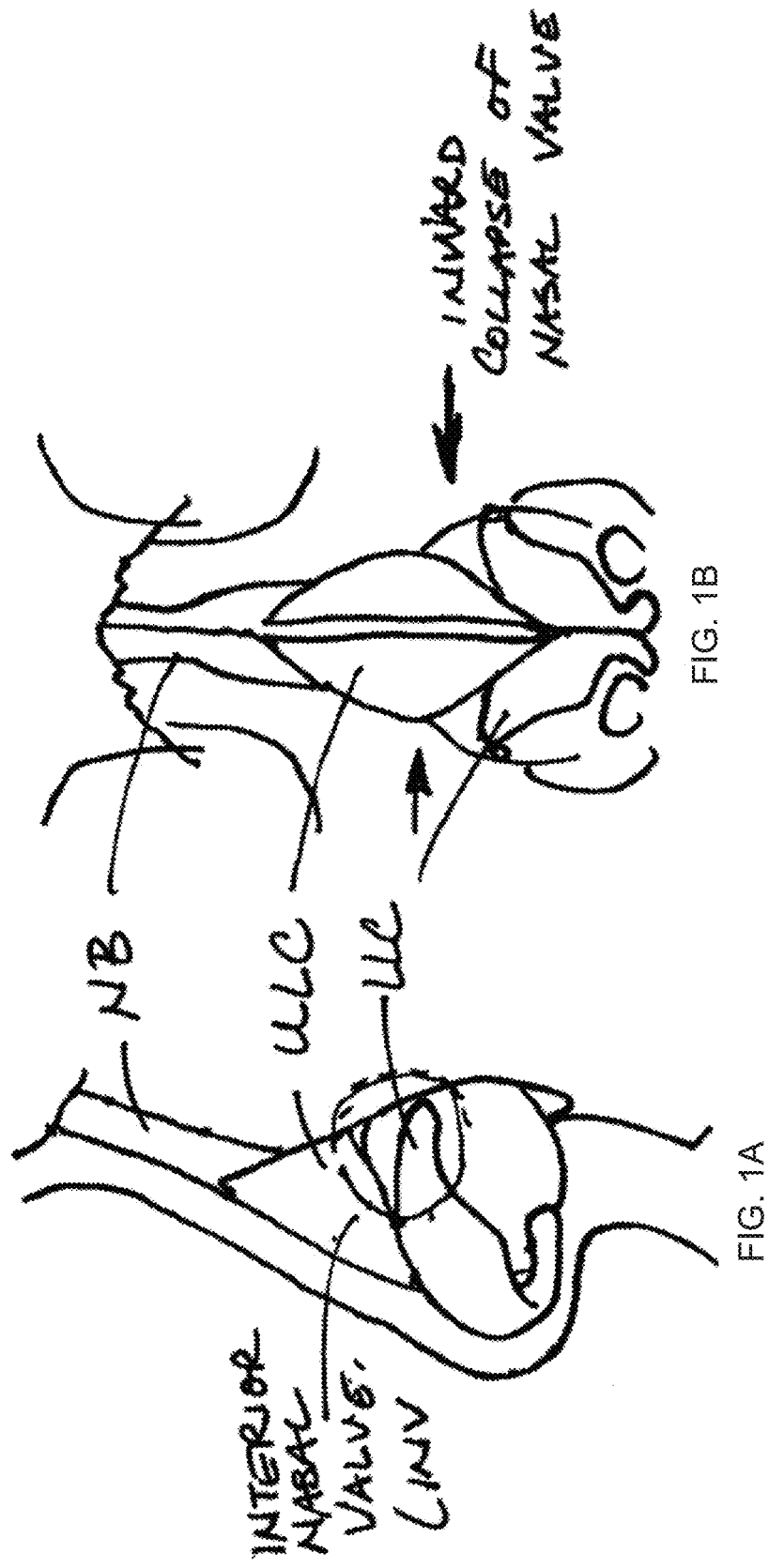

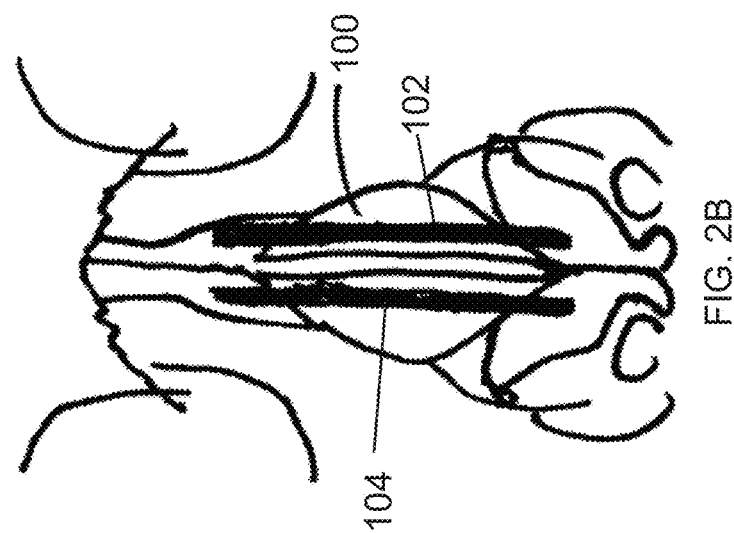
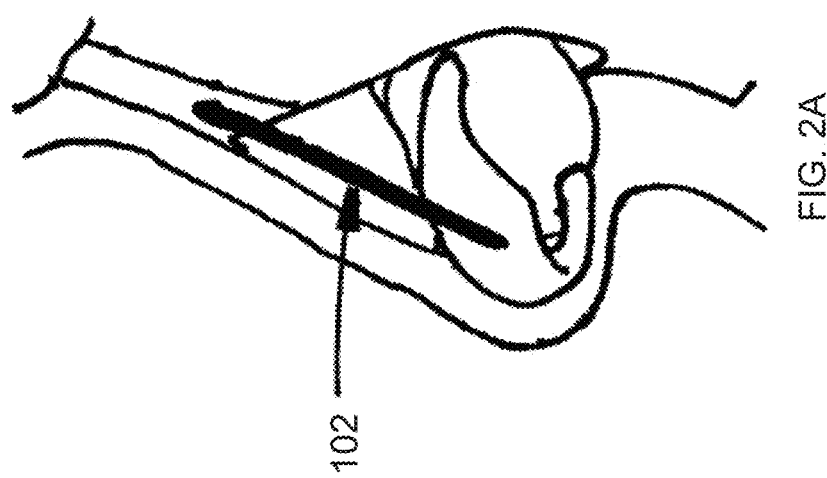

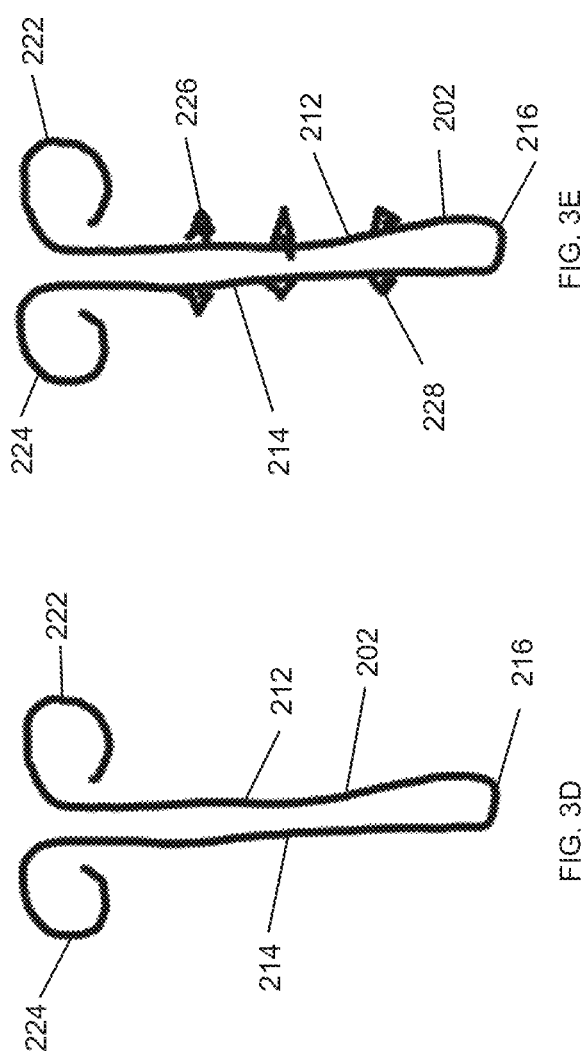

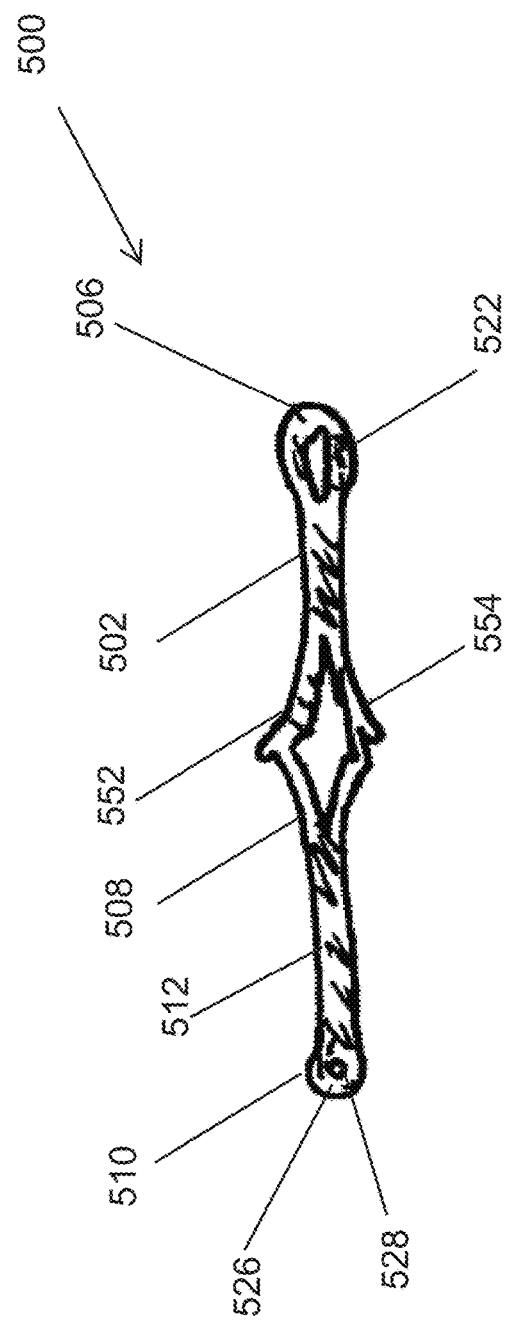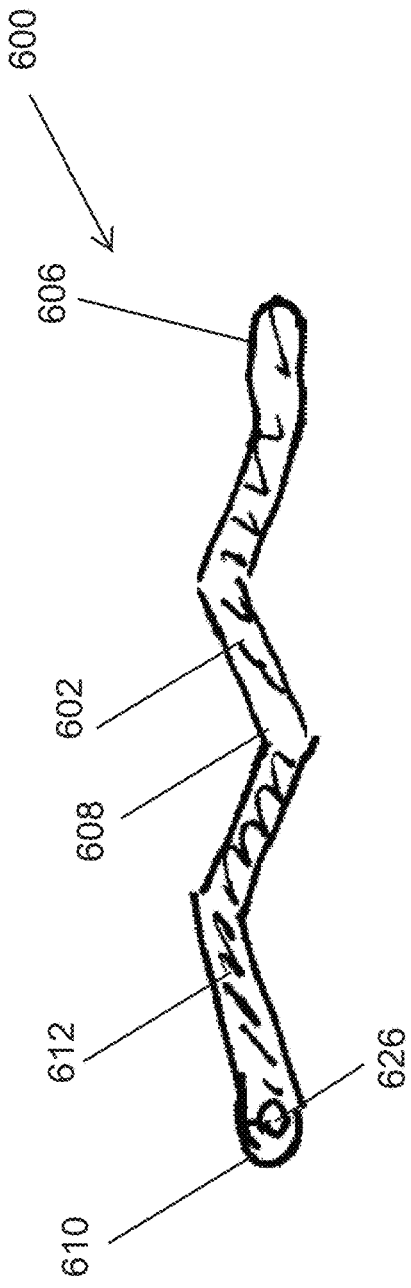
FIG. 6
FIG. 7

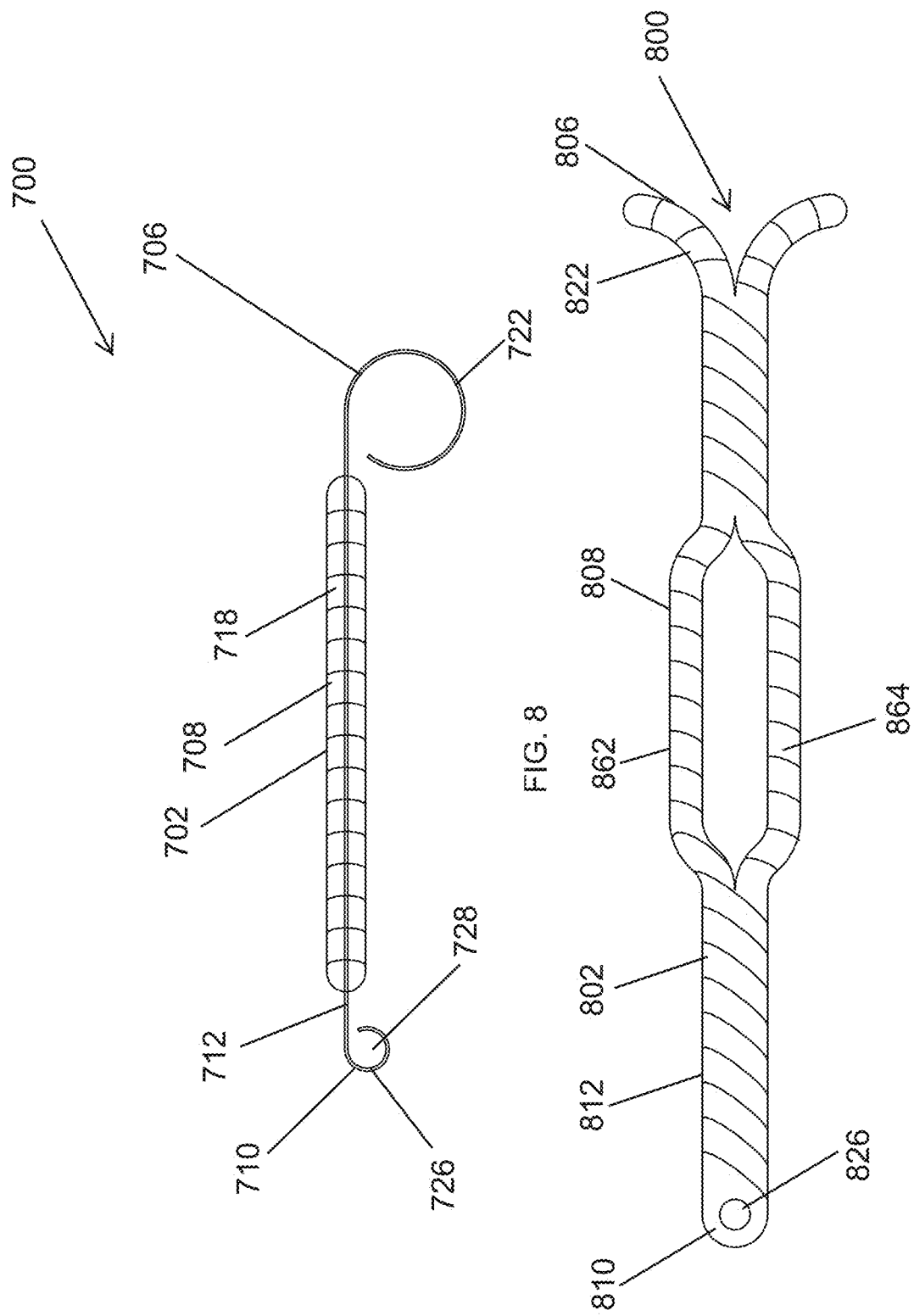

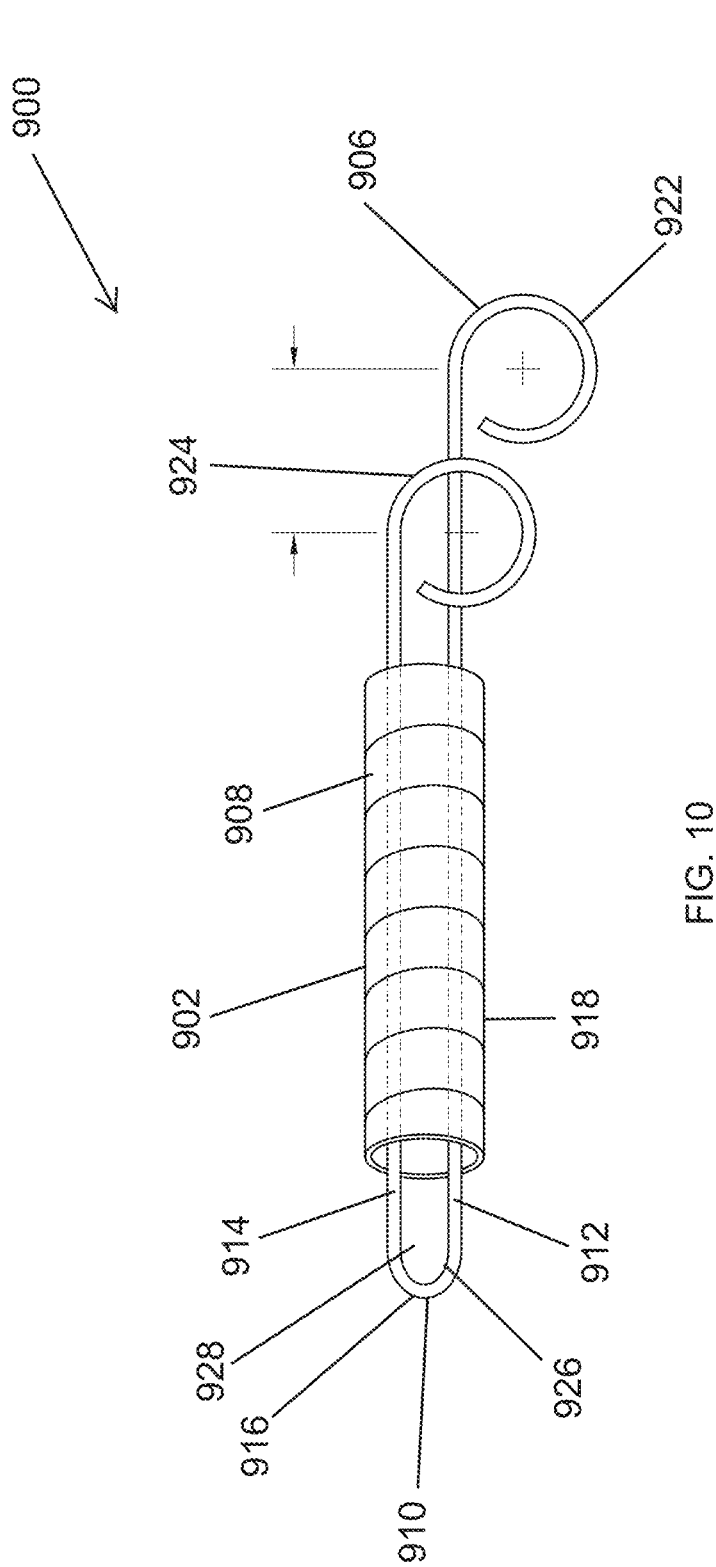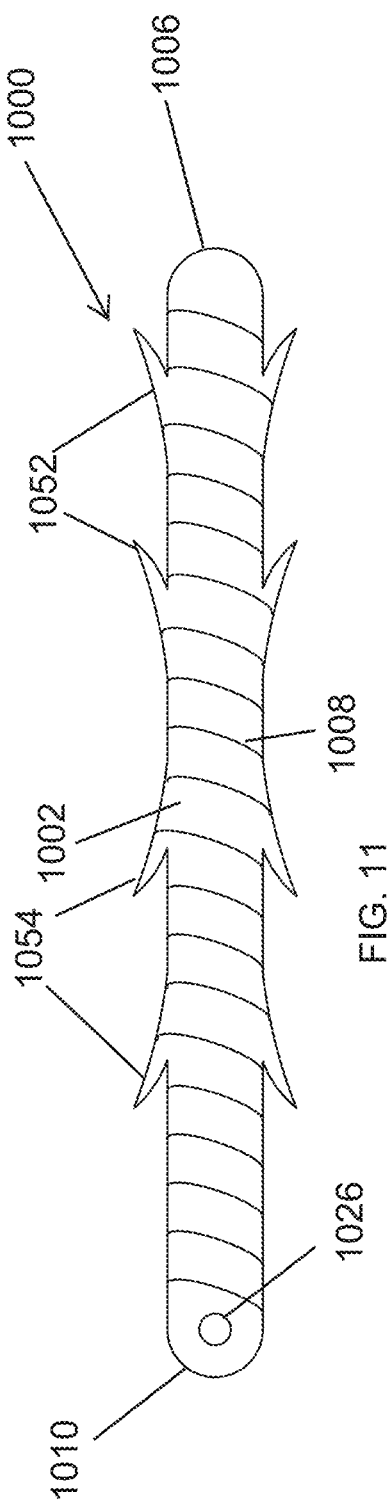

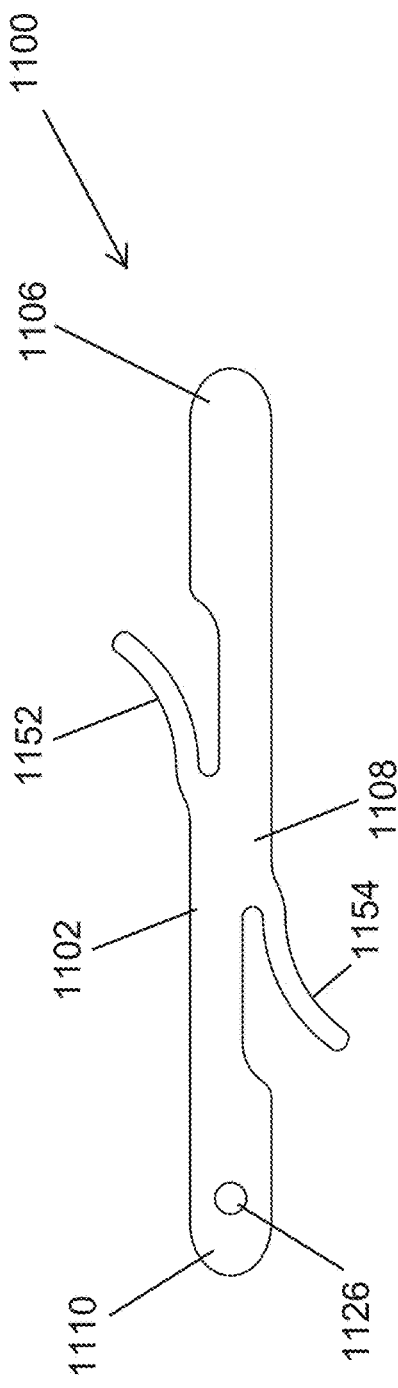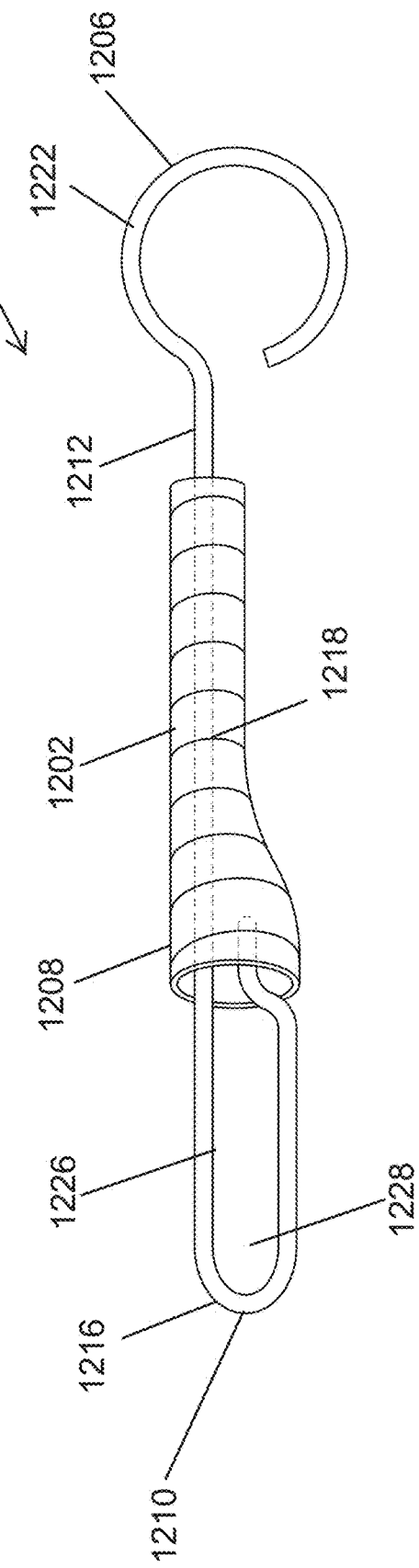
FIG. 12
FIG. 13

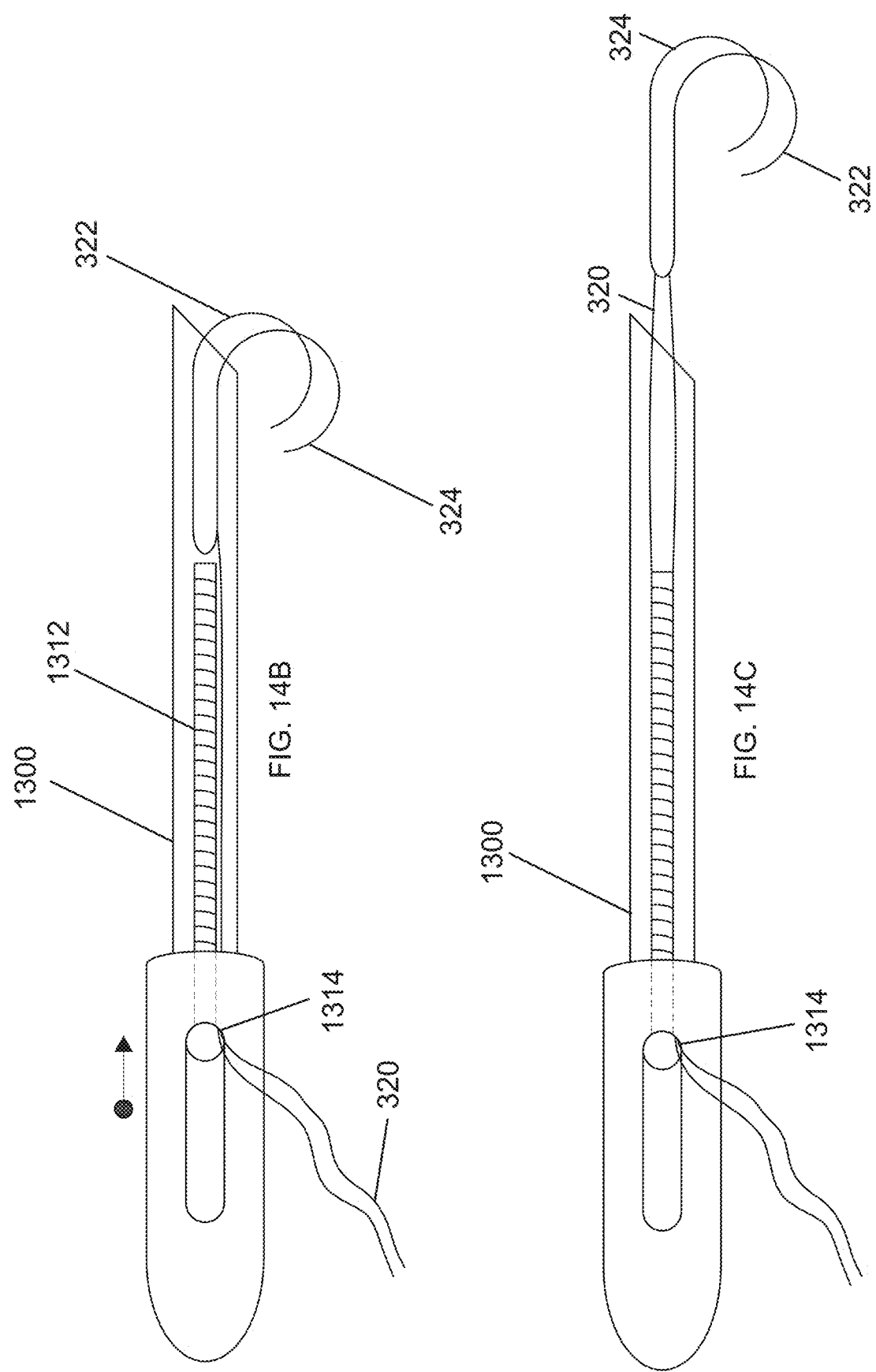

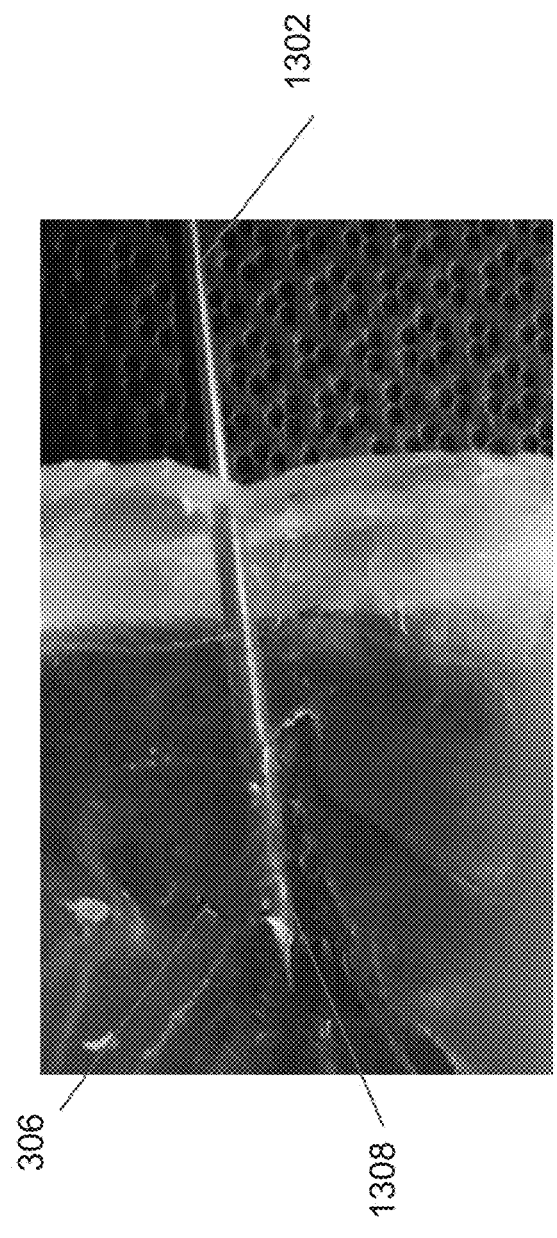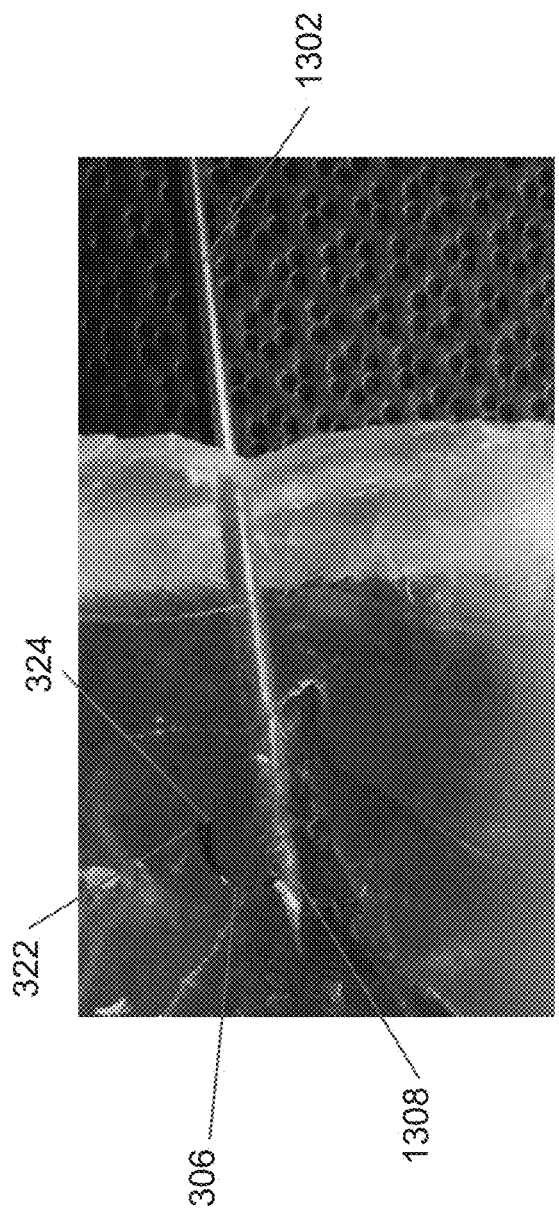

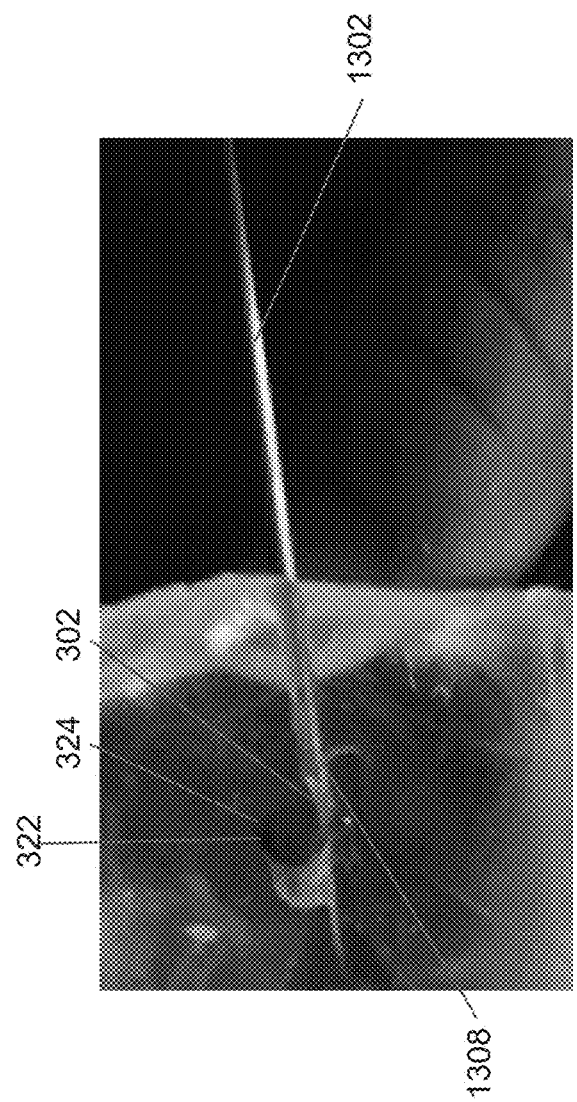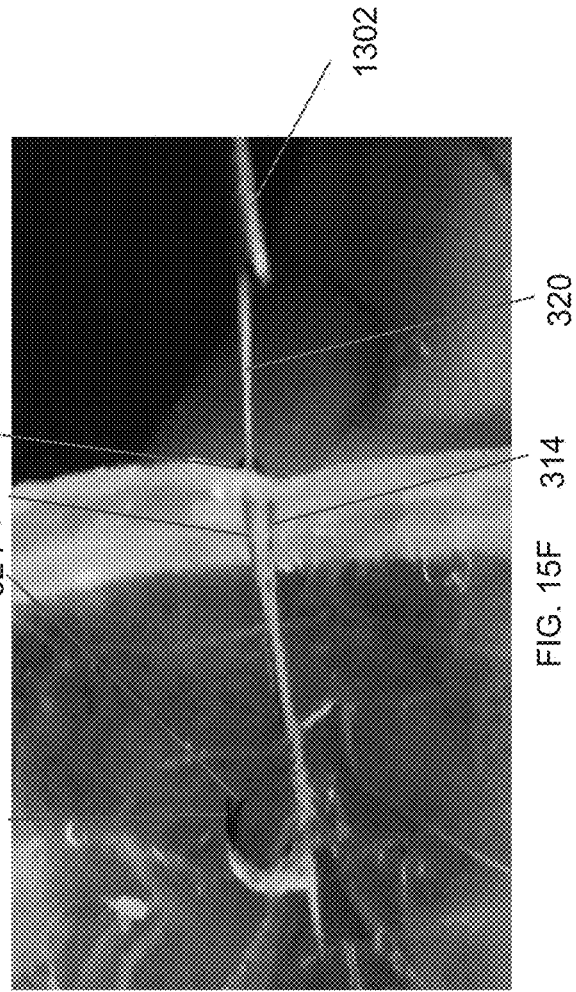

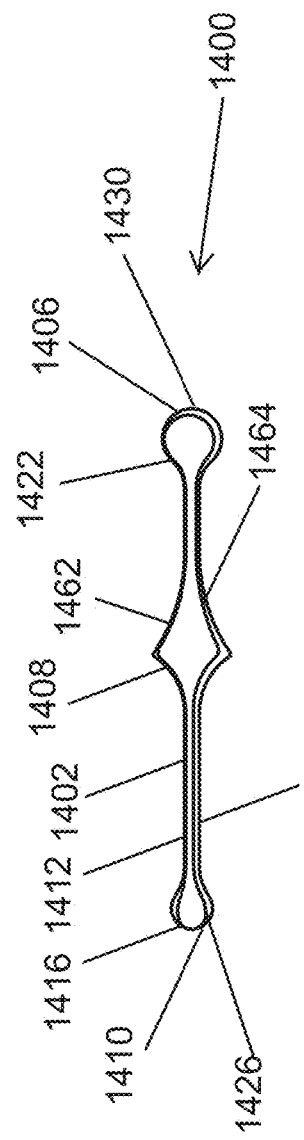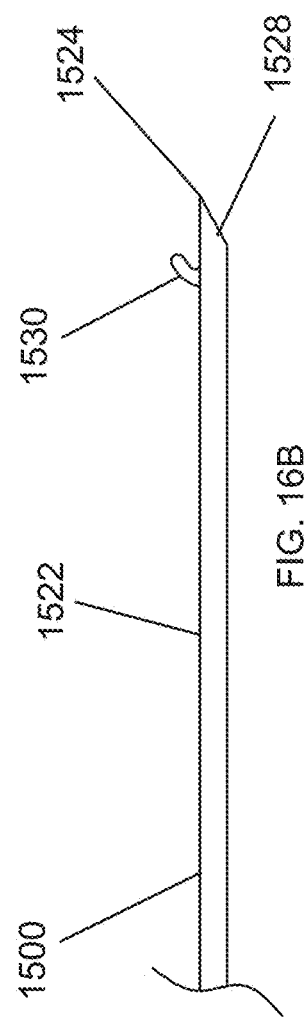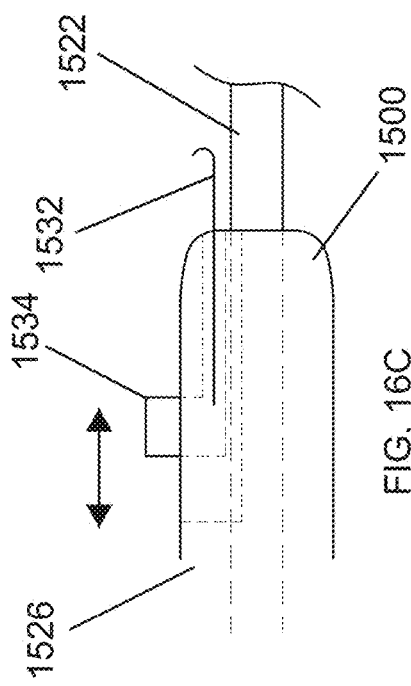

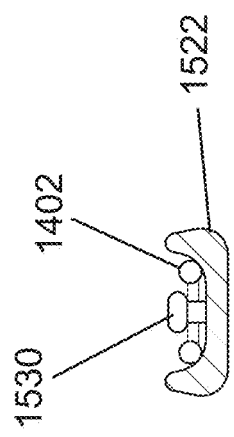
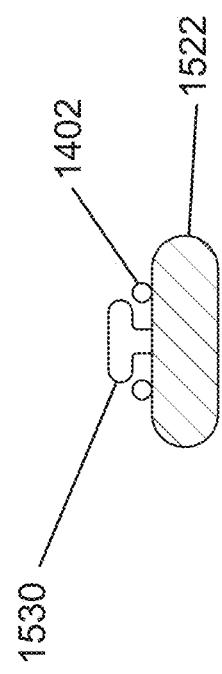
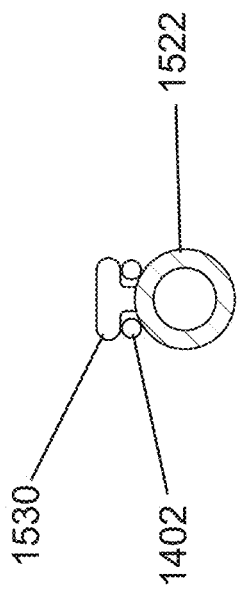

SYSTEMS AND METHODS FOR NASAL SUPPORT

PRIORITY CLAIM

This application claims the benefit under 35 U.S.C. § 119(e) as a nonprovisional application of U.S. Provisional App. No. 62/729,032 filed on Sep. 10, 2018, which is hereby incorporated by reference in its entirety.

BACKGROUND

Field

In some aspects, the invention relates generally to an implant for the treatment of nasal valve collapse. Disclosed herein are systems and methods for stabilizing the nasal valve including the use of a cartilage support implant.

Description of the Related Art

One cause of nasal airway obstruction is nasal valve collapse which occurs when the nasal cartilages fail to provide adequate support. During inspiration for healthy patients, the nasal cartilage functions to support the open nasal passages. The nasal cartilage limits or reduces valve collapse. However, if the nasal cartilages become weakened, then the lateral nasal cartilages can collapse and obstruct the nasal airways. Collapse can be caused by various structures including but not limited to the nasal septum, nasal turbinates, and lateral cartilages.

In many cases, there is a need to provide support to the nasal cartilages to prevent this collapse. There remains a need for improved methods and devices for treating various conditions, including but not limited to nasal airway obstruction. There is also a need for improved devices and methods for delivering and removing support structures from the cartilage. Specifically with respect to current methods for providing support, there is a need to maintain support in the cartilage, provide sufficient anchoring for the support, improve the surgeon's range and ability to precisely locate and orient the support including any anchors, and improve the ability of surgeons to properly remove the support.

SUMMARY

The present disclosure provides cartilage support system as well as methods for deploying and retrieving the cartilage support system.

In some embodiments, a system and method for supporting a nasal valve is provided. The method can include providing a first elongate body and a second elongate body sized to reside within the nose of a patient. The method can include placing the first elongate body adjacent to a first nasal bone, wherein the first elongate body comprises a first anchor at an end of the first elongate body configured to be positioned closer to the first nasal bone. The method can include placing the second elongate body adjacent to a second nasal bone, wherein the second elongate body comprises a second anchor at an end of the second elongate body configured to be positioned closer to the second nasal bone. In some embodiments, the first elongate body and the second elongate body anchor within the nasal tissue and provide support to the nasal valve, wherein the implant is made of biodegradable or bioresorbable material.

In some embodiments, the first anchor curves between about 5 and about 360 degrees. In some embodiments, the second anchor curves between about 5 and about 360 degrees. In some embodiments, the first elongate body comprises an additional anchor feature along the length of the first elongate body. In some embodiments, the additional anchor feature comprises a spike. In some embodiments, the implant is a stabilizing stent that extends between the nasal bone and the lower lateral cartilage. In some embodiments, the first elongate body is removable. The method can include engaging two anchors of each elongate body with the anatomy of the patient. The method can include a single point of anchoring. In some embodiments, the first elongate body includes a coating to promote tissue ingrowth. In some embodiments, the first elongate body extends along the midline prominence of the nose. In some embodiments, the first elongate body is configured to be straightened during implantation within the nose of the patient. In some embodiments, the first elongate body is configured to be trimmed while straightened.

In some embodiments, a cartilage support implant is provided. The cartilage support implant can include a first elongate body configured to reside within the nose of a patient, the first elongate body comprising a first end comprising an anchor portion configured to have a compressed shape and an expanded shape, wherein the expanded shape comprises a curved shape extending toward a second end of the elongate body, opposite the first end, thereby forming a first anchor, the expanded shape configured to anchor the first elongate body. In some embodiments, the implant is made of bioabsorbable material. In some embodiments, the first elongate body is configured to transition between the expanded shape and the compressed shape.

In some embodiments, the first anchor curves between about 5 and 360 degrees. In some embodiments, the expanded shape comprises a second curved shape extending toward a second end of the elongate body, opposite the first end, thereby forming a second anchor. In some embodiments, the first anchor curves between about 5 and 360 degrees, wherein the second anchor curves between about 5 and 360 degrees. In some embodiments, the first elongate body comprises an additional anchor feature along the length of the first elongate body. In some embodiments, the additional anchor feature comprises a spike. In some embodiments, the first elongate body is configured to be trimmed for length when in the compressed shape.

BRIEF DESCRIPTION OF THE DRAWINGS

FIGS. 1A-1B illustrate a schematic view of the nasal passageways.

FIGS. 2A-2B illustrate an embodiment of a cartilage support implant.

FIGS. 3A-3E illustrate an embodiment of a cartilage support implant.

FIGS. 4-13 illustrate embodiments of a cartilage support implant.

FIGS. 14A-14C illustrate an embodiment of a cartilage support delivery system and a cartilage support implant.

FIGS. 15A-15L illustrate an embodiment of a cartilage support delivery system and a cartilage support implant.

FIGS. 16A-16I illustrate an embodiment of a cartilage support delivery system and a cartilage support implant.

DETAILED DESCRIPTION

Figure 3B:
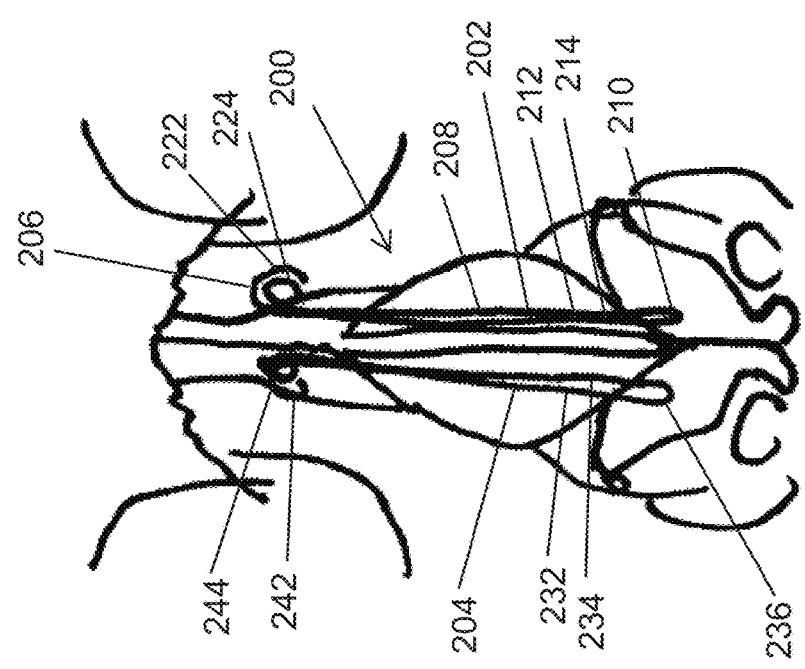

FIG. 1A illustrates a side view of the structural anatomy of the nose. FIG. 1B is a front view. The nasal bones (NB) are illustrated. The nasal bones are two small, oblong bones that form the bridge of the nose. The upper lateral cartilage (ULC) and the lower lateral cartilage (LLC) are also illustrated. The upper lateral cartilage is situated below the nasal bone. The upper lateral cartilage has a flattened, triangular shape. The lower lateral cartilage is also known as the greater alar cartilage. The lower lateral cartilage is situated below the upper lateral cartilage. The upper lateral cartilage has a thin, flexible plate shape, and is bent onto itself.

The nasal valve provides airflow resistance, which is important for pulmonary function. The nasal valve includes internal and external portions. The external nasal valve dilates during inspiration and is formed by the columella, the nasal floor, and the lower lateral cartilage. The internal nasal valve provides greater resistance and is typically the narrowest part of the nasal passage. The internal nasal valve is bounded by the septum, the upper lateral cartilage, and the pyriform aperture. The internal nasal valve is a segment between the septum and the caudal margin of the upper lateral cartilage. The angle between the septum and the caudal margin of the upper lateral cartilage is typically between about 10 degree and 15 degrees. Collapse of the internal nasal valve occurs when this angle is decreased.

The most common causes of nasal valve collapse include deviations of the septum, trauma, deviations in the cartilage including twisted cartilage or the absence of cartilage, over-resection which weakens the cartilage, inflammation, and/or deformities in other structures including the pyriform aperture. Rhinoplasty is also known to damage the internal nasal valve. With nasal valve insufficiency, upon inspiratory efforts, the internal nasal valve collapses inwardly (medially) and obstructs the nasal airway.

A recent clinical study has shown that placing a bioresorbable stent or splint across the upper lateral cartilage and the lower lateral cartilage and along the nasal bone can reduce symptoms of nasal valve collapse. As a mechanical stabilizing structure, the benefits of the stent are reduced as it resorbs. Longer-lasting and more efficacious systems and methods are needed.

FIGS. 2A-2B illustrate an embodiment of a cartilage support implant 100. The cartilage support implant 100 can function as a stabilizing stent. The cartilage support implant 100 can be a minimally invasive implantable stent that can be removable. The cartilage support implant 100 can be non-bioresorbable, or bioresorbable in other embodiments. The cartilage support implant 100 can provide sufficient support to reduce or prevent nasal valve collapse. The cartilage support implant 100 can comprise a first elongate body 102 and a second elongate body 104. In some embodiments, the first elongate body 102 and the second elongate body 104 are substantially similar, similar, or identical. In some embodiments, the first elongate body 102 and the second elongate body 104 are different. For instance, the first elongate body 102 and the second elongate body 104 can have one or more different dimensions, such as length, width, height, or shape including cross-sectional shape, or material. The elongate bodies could be discrete and unconnected as shown, or connected to one another in other embodiments.

Each elongate body 102, 104 can be sized to span between the upper nasal bone and the lower lateral cartilage. Each elongate body 102, 104 can include an upper portion configured to be placed near the nasal bone. Each elongate body 102, 104 can include a middle portion configured to be placed near the upper lateral cartilage. Each elongate body 102, 104 can include a lower portion configured to be placed near the lower lateral cartilage. The elongate body 102, 104 can have any desired cross-sectional shape (e.g., round, circular, elliptical, polygonal, rectangular, etc.). The elongate body 102, 104 can be solid. The elongate body 102, 104 can be cannulated or tubular. The elongate body 102, 104 can be rigid or flexible. The elongate body 102, 104 can be elastic or inelastic. The elongate body 102, 104 can be formed of one, two, or more materials. The elongate body 102, 104 can be formed from a metal, plastic, or any other biocompatible material.

The elongate bodies described herein can be formed from a bioresorbable material. The elongate body can be formed from a bioresorbable scaffold. The elongate body can be formed from a biodegradable material. The elongate body can be formed from any naturally dissolving material. The elongate body can be formed from any material that may dissolve or be absorbed in the body. The elongate body can be formed from, for example, polylactic acid (PLLA), self-reinforced polylatic acid (SR PLLA), lactide and glycolide, polyglycolide or poly(glycolic acid) (PGA) and/or combinations thereof. In some embodiments, the biodegradable or bioabsorbable material selected from the group consisting of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester; poly (amino acids), and poly(alpha-hydroxy acid). The elongate body can be formed from bioresorbable metals such as magnesium based metals or alloys, or magnesium based metals or alloys, or zinc based metals or alloys. All implant embodiments can include a bioresorbable material option.

The elongate bodies described herein can be selected based on a length measurement. The user can determine the length of the implant based on measurements of the patient's anatomy. The length of the implant can be determined based on the length of the internal nasal valve. The length of the implant can be determined based on the length to the nasal bones. The length of the implant can be determined based on the length between the upper nasal bone and the lower lateral cartilage. The length of the implant can be determined based on the length of the upper lateral cartilage. The length of the implant can be determined based on any landmarks within the nasal passage.

In some methods, the user selects an appropriate length implant to place in the delivery system for implantation. In some methods, the user selects an appropriate length implant based on the size of the implant. In some methods, the user selects an appropriate length implant based on the shape of the implant. In some methods, the user selects an appropriate length implant based on the configuration of the anchors. In some methods, the user select an appropriate length implant based on an evaluation of the patient's anatomy.

In some methods, the user selects an appropriate length implant by trimming the implant to a desired length before delivery. In some methods, the user straightens the implant in order to trim the implant. In some methods, the user trims the implant without straightening. In some methods, the user bends the implant to change the length of the implant. In some methods, the user straightens the implant to change the length of the implant. In some methods, the user straightens the anchors to change the length of the implant. In some methods, the user further curves the anchors to change the length of the implant.

In some methods, the user forms the implant before implantation. In some methods, the implant arrives preformed to the user. In some methods, the implant is formed from a single length of material. In some methods, the implant is cut, trimmed, or otherwise reduced to an appropriate length and/or other dimension before forming the implant shape. In some methods, the implant is cut, trimmed, or otherwise reduced to an appropriate length after the implant shape is formed. In some methods, the elongate body is configured to transition between the expanded shape and the compressed shape. In some methods, the elongate body is configured to be trimmed when in a compressed or straightened shape.

Figure 3A:
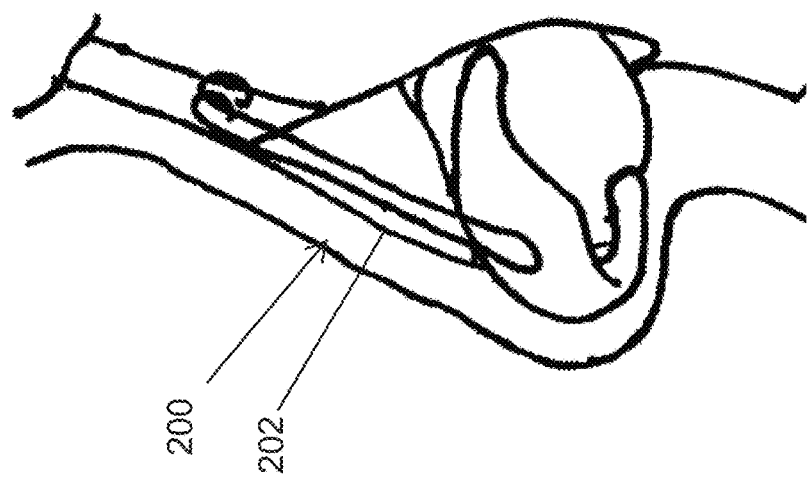

FIGS. 3A-3B illustrate an embodiment of a cartilage support implant 200. The cartilage support implant 200 comprises a first elongate body 202 and a second elongate body 204. In some embodiments, the cartilage support implant 200 comprises only one elongate body. In some embodiments, the cartilage support implant 200 comprises a plurality of elongate bodies (e.g., two, three, four, five, six, etc.). Each elongate body 202, 204 can include a first end 206 configured to be placed near the nasal bone. Each elongate body 202, 204 can include a middle portion 208 configured to be placed near the upper lateral cartilage. Each elongate body 202, 204 can include a second end 210 configured to be placed near the lower lateral cartilage. The first end 206 can include one or more anchors, as describe herein.

Figure 3C:
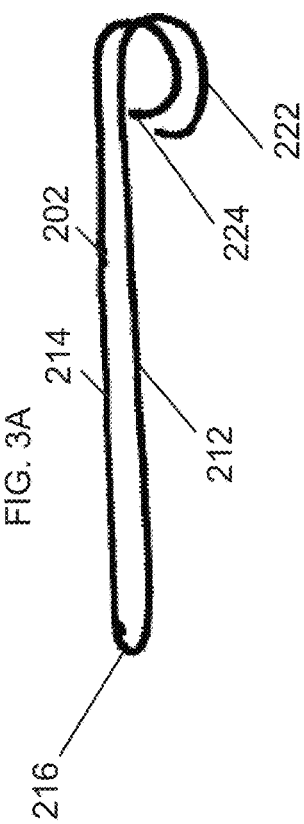

FIG. 3C illustrates the first elongate body 202. FIG. 3D illustrates another view of the first elongate body 202. The second elongate body 204 can include any of the features of elongate body 202. The first elongate body 202 can include a U-shaped configuration. The first elongate body 202 includes a first strut 212 that extends the length of the elongate body 202. The elongate body 202 includes a second strut 214 that extends the length of the elongate body 202. The elongate body 202 can include a distal curve 216 that connects the first strut 212 and the second strut 214. The first strut 212 and the second strut 214 can lie on the same plane. The first strut 212, the distal curve 216, and the second strut 214 can lie on the same plane. The first strut 212 and the second strut 214 can be skewed. The distal curve 216 can twist such that the first strut 212 and the second strut 214 are skewed.

The first elongate body 202 can include a lower portion. The lower portion can form a generally U-shape. The lower portion can include at least one bend or curve. The lower portion can include the distal curve 216. The first strut 212 can include a lower portion. The lower portion of the first strut 212 can extend from the distal curve 216. The second strut 214 can include a lower portion. The lower portion of the second strut 214 can extend from the distal curve 216. The lower portion of the first strut 212 and the second strut 214 can be parallel. The lower portion of the first strut 212 and the second strut 214 can be skewed. The lower portion of the first strut 212 and the second strut 214 can be disposed at an acute angle. The lower portion of the first strut 212 and the second strut 214 can be generally straight. The lower portion of the first strut 212 and the second strut 214 can include a curve or a bend.

The first elongate body 202 can include an upper portion. The upper portion can form a generally T-shape. The upper portion can include at least one bend or curve. The upper portion can include the first anchor 222 and the second anchor 224. The first strut 212 can include an upper portion. The upper portion of the first strut 212 can extend outward from the lower portion of the first strut 212. The second strut 214 can include an upper portion. The upper portion of the second strut 214 can extend outward from the lower portion of the second strut 214. The upper portion of the first strut 212 and the second strut 214 can be parallel. The upper portion of the first strut 212 and the second strut 214 can be skewed. The upper portion of the first strut 212 and the second strut 214 can be disposed at an acute angle. The upper portion of the first strut 212 and the second strut 214 can be generally curved. The upper portion of the first strut 212 and the second strut 214 can be the same or similar. The upper portion of the first strut 212 and the second strut 214 can be mirror images.

The first anchor 222 can be formed from the proximal end of the first strut 212 and the second anchor 224 can be formed from the proximal end of the second strut 214. In some embodiments, only the first strut 212 forms the anchor 222. In some embodiments, only the second strut 214 forms the anchor 224. The anchors 222, 224 form a rounded top surface of each strut 212, 214. The anchors 222, 224 can exert a biasing force on surrounding structures, such as tissue, cartilage, and bone. The anchors 222, 224 can resist movement of the elongate body. In some embodiments, the anchors 222, 224 penetrate the nasal bone. In some embodiments, the anchors 222, 224 do not penetrate the nasal bone. In some embodiments, positioning the anchors 222, 224 against the nasal bone provides enough stability without penetrating the nasal bone. Each anchor 222, 224 can be designed to engage a target location within the anatomical structure.

In some embodiments, the first anchor 222 extends below the first strut 212, as shown in FIG. 3C. The first anchor 222 is coaxial with the first strut 212. In some embodiments, the second anchor 224 extends below the second strut 214 as shown in FIG. 3C. The second anchor 224 is coaxial with the second strut 214. In some embodiments, the first anchor 222 extend above the first strut 212. The first anchor 222 is coaxial with the first strut 212. In some embodiments, the second anchor 224 extends below the second strut 214. The second anchor 224 is coaxial with the second strut 214. In some embodiments, the first anchor 222 and the first strut 212 lie generally within a first plane. In some embodiments, the second anchor 224 and the second strut 214 lie generally within a second plane. In some embodiments, the first plane and the second plane are parallel.

In some embodiments, the first anchor 222 extends to the right from the first strut 212. The first anchor 222 is laterally offset with the first strut 212. In some embodiments, the second anchor 224 extends to the left of the second strut 214. The second anchor 224 is laterally offset with the second strut 214. In some embodiments, the first anchor 222, the second anchor 224, the first strut 212 and the second strut 214 lie generally within the same plane.

In some embodiments, the first anchor 222 extends to the right and downward from the first strut 212. The first anchor 222 is laterally offset and skewed with respect to the first strut 212. In some embodiments, the second anchor 224 extends to the left and downward of the second strut 214. The second anchor 224 is laterally offset and skewed with respect to the second strut 214. In some embodiments, the first anchor 222 and the first strut 212 lie generally within a first plane. In some embodiments, the second anchor 224 and the second strut 214 lie generally within a second plane. In some embodiments, the first plane and the second plane are skewed.

In some embodiments, the first anchor 222 forms a curve. The first anchor 222 can form a portion of a circle. The first anchor 222 can curve between 5 and 360 degrees. The first anchor 222 can curve 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, 180 degrees, 185 degrees, 190 degrees, 195 degrees, 200 degrees, 205 degrees, 210 degrees, 215 degrees, 220 degrees, 225 degrees, 230 degrees, 235 degrees, 240 degrees, 245 degrees, 250 degrees, 255 degrees, 260 degrees, 265 degrees, 270 degrees, 275 degrees, 280 degrees, 285 degrees, 290 degrees, 295 degrees, 300 degrees, 305 degrees, 310 degrees, 315 degrees, 320 degrees, 325 degrees, 330 degrees, 335 degrees, 340 degrees, 345 degrees, 350 degrees, 355 degrees, 360 degrees, or any range of the foregoing values.

In some embodiments, the second anchor 224 forms a curve. The second anchor 224 can form a portion of a circle. The second anchor 224 can curve between 5 and 360 degrees. The first anchor 222 can curve 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, 180 degrees, 185 degrees, 190 degrees, 195 degrees, 200 degrees, 205 degrees, 210 degrees, 215 degrees, 220 degrees, 225 degrees, 230 degrees, 235 degrees, 240 degrees, 245 degrees, 250 degrees, 255 degrees, 260 degrees, 265 degrees, 270 degrees, 275 degrees, 280 degrees, 285 degrees, 290 degrees, 295 degrees, 300 degrees, 305 degrees, 310 degrees, 315 degrees, 320 degrees, 325 degrees, 330 degrees, 335 degrees, 340 degrees, 345 degrees, 350 degrees, 355 degrees, 360 degrees, or any range of the foregoing values.

FIG. 3E illustrates the first elongate body 202 with one or more additional anchoring features. The first strut 212 can include one or more anchoring features 226. The second strut 214 can include one or more anchoring features 228. In some embodiments, the anchoring features 226, 228 are passive anchors. In some embodiments, the anchoring features 226, 228 are spikes or barbs. In some embodiments, the anchoring features 226, 228 are wedges. In some embodiments, the anchoring features 226, 228 prevent movement in one direction but allow movement in another direction.

In some embodiments, the anchoring features 226, 228 of the first elongate body 202 are substantially similar, similar, or identical. In some embodiments, the anchoring features 226, 228 of the first elongate body 202 are different. For instance, the anchoring features 226, 228 can have one or more different dimensions, such as length, width, height, or shape including cross-sectional shape, or material. The anchoring features 226, 228 can be mirror image anchors. The anchoring features 226, 228 can be symmetrical.

In some embodiments, the anchors 222, 224 of the first elongate body 202 are substantially similar, similar, or identical. In some embodiments, the anchors 222, 224 of the first elongate body 202 are different. For instance, the anchors 222, 224 can have one or more different dimensions, such as length, width, height, or shape including cross-sectional shape, or material. The anchors 222, 224 can be mirror image anchors. The anchors 222, 224 can be symmetrical.

The anchor 222 can extend in a first direction away from the proximal end of the first strut 212, toward the distal curve 216, and in a second direction toward the first strut 212. The anchor 224 can extend in a first direction away from the proximal end of the second strut 214, toward the distal curve 216, and in a second direction toward the second strut 214. Other configurations are contemplated. The anchors 222, 224 can form a curve with a constant radius. The anchors 222, 224 can form a complete curve. The anchors 222, 224 can form a helix. The anchors 222, 224 can form an s-shaped curve. The anchors 222, 224 can form a u-shaped curve. The anchors 222, 224 can form a j-shaped curve. In some embodiments, the elongate body 202 can be formed as a single piece. The anchors 222, 224, the struts 212, 214, and the distal curve 216 can be continuous.

The second elongate body 204 can include any of the features of the first elongate body 202 shown in FIG. 2B. The elongate body 204 can include a third strut 232, a fourth strut 234, and a distal curve 236. The elongate body 204 can include a third anchor 242 and a fourth anchor 244. In some embodiments, the anchors 242, 244 of the second elongate body 204 are substantially similar, similar, or identical. In some embodiments, the anchors 222, 224 of the first elongate body 202 and the anchors 242, 244 of the second elongate body 204 are substantially similar, similar, or identical.

The elongate body 202, 204 can be formed from a metal, plastic, or any other biocompatible material. The elongate body 202, 204 can be removable, as described herein. The anchors 222, 224, 242, 244 can include a delivery configuration. The delivery configuration can be a low-profile configuration. For instance, the anchors 222, 224, 242, 244 can be flattened or straightened for delivery. The anchors 222, 224, 242, 244 can include a deployed configuration. The deployed configuration is shown in FIG. 3A-3B. The anchors 222, 224, 242, 244 can form a different shape than the delivery configuration. The anchors 222, 224, 242, 244 can assume a pre-formed shape. In some embodiments, the anchors 222, 224, 242, 244 can comprise a shape memory material. The anchors 222, 224, 242, 244 can include a pre-formed shape with at least one curve. The anchors 222, 224, 242, 244 can be designed to provide attachment of the first elongate body 202 and the second elongate body 204 to the respective nasal bones. The anchors 222, 224, 242, 244 can comprise a nitinol alloy. The anchors 222, 224, 242, 244 can comprise any bio-inert material, such as any material typical of biological implants, including stainless steel, titanium, and polymers such as PEEK. In some embodiments, the entire elongate body 202, 204 comprises a nitinol alloy. In some embodiments, the anchors 222, 224, 242, 244 are self-expanding. In some embodiments, the anchors 222, 224, 242, 244 are removed from a constraint and assume the deployed configuration. The constraint can be a delivery system such as a cannula or inserter, as described herein.

In some embodiments, the anchors 222, 224, 242, 244 have a pre-determined curved shape. The anchors 222, 224, 242, 244 can be formed of a shape memory material. The anchors 222, 224, 242, 244 can be designed to be spring-loaded. When delivered to the target location, the anchors 222, 224, 242, 244 can rapidly change shape from a low-profile or straightened shape to the pre-determined curved shape. In some embodiments, the anchors 222, 224 of the first elongate body 202 are designed to be deployed simultaneously. In some embodiments, the anchors 242, 244 of the second elongate body 204 are designed to be deployed simultaneously. In some embodiments, two or more anchors 222, 224, 242, 244 are designed to be deployed simultaneously. In some embodiments, the anchors 222, 224 of the first elongate body 202 are designed to be deployed separately or independently. In some embodiments, two or more anchors 222, 224, 242, 244 are designed to be deployed separately or independently.

Each elongate body 202, 204 can be a metallic or plastic removable stent. Each elongate body 202, 204 can include one or more anchors 222, 224, 242, 244. The elongate body 202, 204 can be stabilized by the nasal bone. The material of the elongate body 202, 204, or a portion thereof, can include NiTi. The elongate body 202, 204, or a portion thereof, can include a circular cross-section. In some embodiments, each strut 212, 214, 232, 234 can include a circular cross-section. The strut 212, 214, 232, 234 can include in some embodiments a diameter or cross-section from about 0.008" to about 0.020" (e.g., 0.008", 0.009", 0.010", 0.011", 0.012", 0.013", 0.014", 0.015", 0.016", 0.017", 0.018", 0.019", 0.020", between 0.005-0.015", between 0.01-0.02", between 0.015-0.025", etc., or ranges incorporating any two of the aforementioned values).

FIGS. 4-13 illustrate embodiments of cartilage support implants. In some embodiments, a cartilage support implant can comprise one elongate body. In some embodiments, a cartilage support implant can comprise two elongate bodies. In some embodiments, a cartilage support implant can comprise two elongate bodies that are similar, substantially similar or identical. In some embodiments, a cartilage support implant can comprise two elongate bodies which are different (e.g., a combination of any two elongate bodies describe herein). In some methods of use, the cartilage support implant is implanted relative to one nasal valve. In some methods of use, the cartilage support implant comprises two elongate bodies which are implanted on opposite sides of the nasal structure as shown in FIGS. 2A-3B. Each elongate body can be implanted in a nasal valve. The elongate bodies can be considered a right elongate body and a left elongate body. The two elongate bodies can be the same or substantially similar. The two elongate bodies can be mirror images (e.g., opposite relative to a common axis). As one example, the anchors of a first elongate body can extend in a first lateral direction, and the anchors of a second elongate body can extend in a second, opposite, lateral direction. FIGS. 4-13 illustrate embodiments of an elongate body of a cartilage support implant. The elongate bodies of FIGS. 4-13 can include any of the features of elongate bodies of any cartilage support implant described herein.

Figure 4:
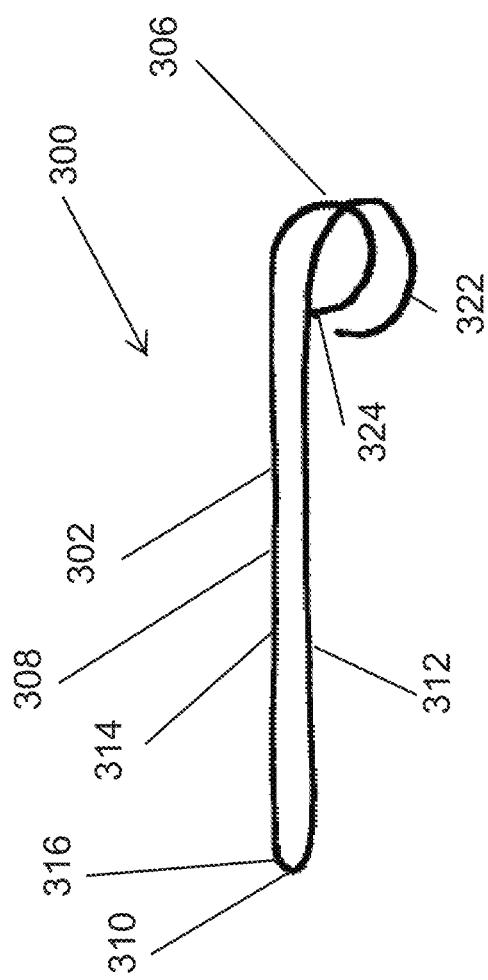

FIG. 4 illustrates an elongate body 302 of a cartilage support implant 300. The cartilage support implant 300 can include a plurality of elongate bodies, as described herein. FIG. 4 illustrates a nasal valve implant concept. The implant includes a support strut and offset anchors. The implant is designed to engage tissue but allow implant removal. The elongate body 302 can include a first end 306. In some embodiments, the first end 306 is configured to be placed near the nasal bone. The first end 306 can include one or more anchors, as describe herein. The elongate body 302 can include a middle portion 308. In some embodiments, the middle portion 308 is configured to be placed near the upper lateral cartilage. The elongate body 302 can include a second end 310. In some embodiments, the second end 310 is configured to be placed near the lower lateral cartilage. Other methods of insertion are contemplated.

The elongate body 302 can include a first strut 312 and a second strut 314. The first strut 312 and the second strut 314 can be parallel. The first strut 312 and a second strut 314 can be connected by a distal curve 316 at the second end 310. The two struts 312, 314 can provide support for the elongate body 302. The two struts 312, 314 can extend along a common axis.

The first strut 312 can include a first anchor 322. The second strut 314 can include a second anchor 324. Each strut 312, 314 can include an anchor 322, 324 at the first end 306. The anchors 322, 324 are offset anchors. The anchors 322, 324 are offset from the common axis of the two parallel struts 312, 314. The anchors 322, 324 can engage tissue but allow removal of the elongate body 302. The two parallel struts 312, 314 can lie in a common plane. In some embodiments, the anchors 322, 324 do not contact the common plane. In some embodiments, the anchors 322, 324 lie entirely on one side of the common plane.

The anchor 322 can extend in a first direction away from the first strut 312, toward the second end 310, and in a second direction toward the first strut 312. The anchor 324 can extend in a first direction away from the proximal end of the second strut 314, toward the second end 310, and in a second direction toward the second strut 314. The anchors 322, 324 curve back toward the second end 310. Upon insertion, the anchors 322, 324 curve back along the length of the elongate body 302. In some embodiments, the elongate body 302 can be formed as a unitary implant. The anchors 322, 324, the struts 312, 314, and the distal curve 316 can be continuously connected.

Figure 5:
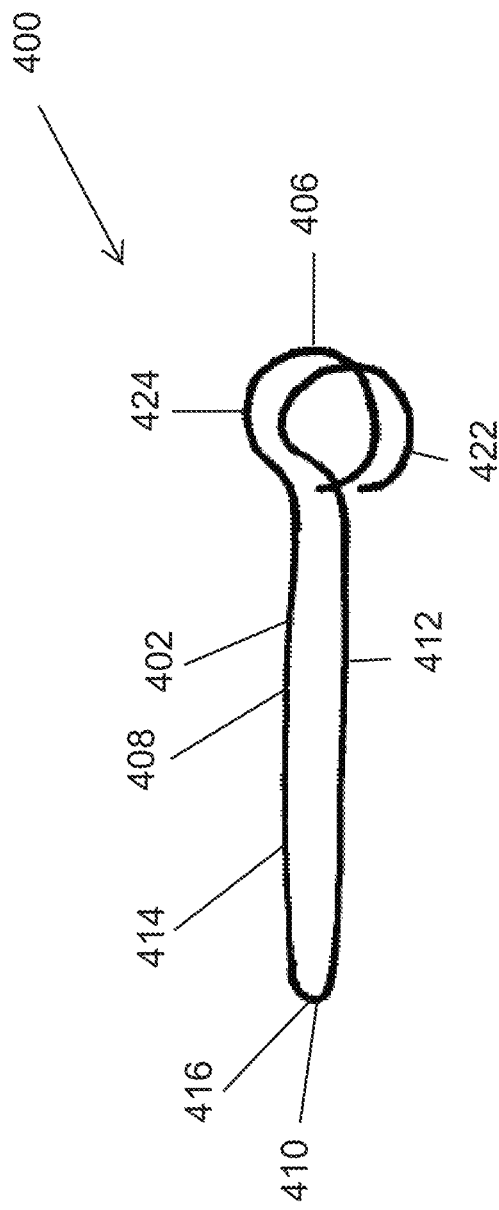

FIG. 5 illustrates an elongate body 402 of a cartilage support implant 400. The cartilage support implant 400 can include a plurality of elongate bodies, as described herein. FIG. 5 illustrates a nasal valve implant concept. The implant includes a support strut and centered anchors. The elongate body 402 can include a first end 406. In some embodiments, the first end 406 is configured to be placed near the nasal bone. The first end 406 can include one or more anchors, as describe herein. The elongate body 402 can include a middle portion 408. In some embodiments, the middle portion 408 is configured to be placed near the upper lateral cartilage. The elongate body 402 can include a second end 410. In some embodiments, the second end 410 is configured to be placed near the lower lateral cartilage.

The elongate body 402 can include a first strut 412 and a second strut 414. The first strut 412 and the second strut 414 can be connected at the second end 410 by a distal curve 416. The first strut 412 and the second strut 414 can be separated at the first end 406. In some embodiments, the struts 412, 414 extend the length of the elongate body 402. In some embodiments, the struts 412, 414 extend a portion of the length of the elongate body 402. In some embodiments, the struts 412, 414 have a fixed distance therebetween at the second end 410. In some embodiments, the struts 412, 414 have a variable distance therebetween at the first end 406. In some embodiments, the first end 406 of the struts 412, 414 can flex toward and away from each other. In some embodiments, the first end 406 of the struts 412, 414 can flex in a common plane. In some embodiments, the first end 406 of the struts 412, 414 can flex to increase the distance therebetween at the first end 406. The two struts 412, 414 can provide axial rigidity for the elongate body 402. The two parallel struts 412, 414 can resist extension.

The first strut 412 can include a first anchor 422. The second strut 414 can include a second anchor 424. Each strut 412, 414 can include an anchor 422, 424 at the first end 406. The anchors 422, 424 are centered anchors. The anchors 422, 424 are centered along a common axis of the struts 412, 414. The two struts 412, 414 can lie in a common plane. In some embodiments, the anchors 422, 424 are centered relative to the common plane. In some embodiments, the anchors 422, 424 lie equally on both sides of the common plane. In some embodiments, each anchor 422, 424 is centered relative to the longitudinal axis of the corresponding strut 412, 424. In some embodiments, each anchor 422, 424 lies equally on both sides of the longitudinal axis of the corresponding strut 412, 414. In some embodiments, the longitudinal axis of the strut 412, 414 extends through a midpoint of the corresponding anchor 422, 424.

The anchor 422 can extend clockwise from the end of the first strut 412. The anchor 422 can extend counterclockwise from the end of the first strut 412. The anchor 424 can extend clockwise from the end of the second strut 414. The anchor 424 can extend counterclockwise from the end of the second strut 414. Each anchor 422, 424 can form a complete circle. Each anchor 422, 424 can form an enclosed perimeter. Each anchor 422, 424 can form a closed shape. Each anchor 422, 424 can form an incomplete circle. Each anchor 422, 424 can form an open perimeter. Each anchor 422, 424 can form an open shape. In some embodiments, the elongate body 402 can be monolithically formed. The anchors 422, 424, the struts 412, 414, and the distal curve 416 can form a single unit.

FIG. 6 illustrates an elongate body 502 of a cartilage support implant 500. The cartilage support implant 500 can include a plurality of elongate bodies, as described herein. FIG. 6 illustrates a nasal valve implant concept. The implant includes a support strut and a nasal bone anchor. The implant includes expandable anchors. The implant includes a tether hole. The implant can be formed from a molded plastic. The elongate body 502 can include a first end 506. In some embodiments, the first end 506 is configured to be placed near the nasal bone. The first end 506 can include one or more anchors, as describe herein. The elongate body 502 can include a middle portion 508. In some embodiments, the middle portion 508 is configured to be placed near the upper lateral cartilage. The elongate body 502 can include a second end 510. In some embodiments, the second end 510 is configured to be placed near the lower lateral cartilage.

The elongate body 502 can include a support strut 512 extending between the first end 506 and the second end 510. The elongate body 502 can include a connection point 526 at the second end 510. The connection point 526 can include an aperture 528 designed to accept a tether (not shown). Other connection points are contemplated. The connection point 526 can include an elongated slot or a round hole. The connection point 526 can include a threaded bore. The connection point 526 can include a hook. The connection point 526 can include a fastener. The connection point 526 can be integrally molded with a tether. The connection point 526 can include an adhesive. The connection point 526 can include a mechanical connection. The connection point 526 can include a snap. The connection point 526 can form a rounded distal surface of the elongate body 502.

The elongate body 502 can include an anchor 522 at the first end 506. The anchor 522 can be designed to engage the nasal bone. The anchor 522 can form a complete circle. The anchor 522 can form an enclosed perimeter. The anchor 522 can form a closed shape. The anchor 522 can form a rounded proximal surface of the elongate body 502. The anchor 522 can be designed to abut, but not penetrate, tissue surrounding the nasal bone.

The elongate body 502 can include one or more middle anchors. The elongate body 502 can include a first middle anchor 552 and a second middle anchor 554. The middle anchors 552, 554 can be designed to engage tissue along the length of the elongate body 502. The anchors 552, 554 can be designed to engage the upper lateral cartilage. The 552, 554 can be disposed in the middle portion 508 of the elongate body 502. The anchors 552, 554 can include one or more barbs to engage tissue. In some embodiments, the anchors 552, 554 can be fixed in position. The anchors 552, 554 can be flexible or rigid.

In some embodiments, the anchors 552, 554 can be expandable. The elongate body 502 can include a central axis. The anchors 552, 554 can expand outward from the central axis. The anchors 552, 554 can expand laterally. The anchors 552, 554 can expand in opposite directions. The anchors 552, 554 can be mirror image anchors. In some embodiments, the anchors 552, 554 can expand from the same location along the length of the elongate body 502. In some embodiments, the anchors 552, 554 can expand from different locations along the length of the elongate body 502.

The anchors 552, 554 can include a low-profile or compressed configuration. For instance, the anchors 552, 554 can be flattened or straightened for delivery. In the compressed configuration, the elongate body 502 can have a first cross-sectional shape. The anchors 552, 554 can include an expanded configuration. The anchors 552, 554 can assume a pre-formed shape. In the expanded configuration, the elongate body 502 can have a second cross-sectional shape. The second cross-sectional shape can be larger than the first cross-sectional shape (e.g., 10% larger, 20% larger, 30% larger, 40% larger, 50% larger, 60% larger, 70% larger, 80% larger, 90% larger, 100% larger, 200% larger, etc.). The elongate body 502 can be formed from any biocompatible material. The elongate body 502, or a portion thereof, can be formed from a molded plastic. In some embodiments, the anchors 552, 554 are formed of a different material than another portion of the elongate body 502.

FIG. 7 illustrates an elongate body 602 of a cartilage support implant 600. The cartilage support implant 600 can include a plurality of elongate bodies, as described herein. FIG. 7 illustrates a zigzag pattern which provides anchoring. The implant can include a tether hole. The elongate body 602 can include a first end 606. In some embodiments, the first end 606 is configured to be placed near the nasal bone. The elongate body 602 can include a middle portion 608. In some embodiments, the middle portion 608 is configured to be placed near the upper lateral cartilage. The elongate body 602 can include a second end 610. In some embodiments, the second end 610 configured to be placed near the lower lateral cartilage.

The elongate body 602 can include a support strut 612 extending between a first end 606 and a second end 610. The elongate body 602 can include a connection point 626 at the second end 610. The connection point 626 can include a tether hole or other connection point, as described herein. The elongate body 602 can include a zig-zag pattern. The zig-zag pattern of the elongate body 602 provides anchoring. In some embodiments, the elongate body 602 does not have a central axis. The zig-zag pattern of the elongate body 602 can be a regular pattern of repeating line segments. The zig-zag pattern of the elongate body 602 can include segments of the same length. The zig-zag pattern of the elongate body 602 can include segments of two or more different lengths. The zig-zag pattern of the elongate body 602 can be an irregular pattern of repeating line segments.

FIG. 8 illustrates an elongate body 702 of a cartilage support implant 700. The cartilage support implant 700 can include a plurality of elongate bodies, as described herein. FIG. 8 illustrates a nasal valve implant concept. The implant can include a molded plastic stiffener. The implant can include NiTi. The implant can include an anchor. The implant can include a tether hole. The elongate body 702 can include a first end 706. In some embodiments, the first end 706 is configured to be placed near the nasal bone. The first end 706 can include one or more anchors, as describe herein. The elongate body 702 can include a middle portion 708. In some embodiments, the middle portion 708 is configured to be placed near the upper lateral cartilage. The elongate body 702 can include a second end 710. In some embodiments, the second end 710 is configured to be placed near the lower lateral cartilage.

The elongate body 702 can include a strut 712. The strut 712 can provide support for the elongate body 710. The strut 712 can have a central longitudinal axis. The strut 712 can include an anchor 722. The anchor 722 can be an offset anchor. The anchor 722 is offset from the central longitudinal axis of the strut 712. The offset shape of the anchor 722 can easily engage tissue but also allow for removal of the elongate body 702, if needed. The anchor 722 can extend downward and away from the strut 712 and then curve back toward the strut 712.

The strut 712 and/or the anchor 722 can include a shape memory material. In some embodiments, the strut 712 and/or the anchor 722 can comprise NiTi. The elongate body 702 can include a sleeve 718. The sleeve 718 can be a coating. The sleeve 718 can surround at least a portion of the strut 712. The sleeve 718 can surround at least a portion of the length of the strut 712. The sleeve 718 can surround at least a portion of the circumference of the strut 712. The sleeve 718 can include a polymer. In some embodiments, the sleeve 718 can comprise a material that is stiffer than the strut 712. In some embodiments, the sleeve 718 can provide added rigidity to the strut 712. In some embodiments, the sleeve 718 is fixed related to the strut 712. The sleeve 718 can be molded onto the strut 712. The sleeve 718 can fully encircle the strut 712 or partially encircle the strut 712. The sleeve 718 can encase the entire length of the strut 712, or a portion thereof. In some embodiments, the sleeve 718 is removable. The sleeve 718 can be disposed within or near the middle portion 708 of the elongate body 702.

The elongate body 702 can include a connection point 726. The connection point 726 can include an aperture 728 designed to accept a tether. The connection point 726 can be at the opposite end of the elongate body 702 as the anchor 722. The connection point 726 can extend clockwise from the strut 712. The connection point 726 can extend counterclockwise from the strut 712. The anchor 722 can extend clockwise from the strut 712. The anchor 722 can extend counterclockwise from the strut 712. The connection point 726 and the anchor 722 can extend in opposite direction.

The anchor 722 and/or the connection point 726 can form a complete or nearly complete circle. The anchor 722 and/or the connection point 726 can form an enclosed perimeter or other closed shape. The closed shape may facilitate retention of the tether within the connection point 726. The anchor 722 and/or the connection point 726 can form an incomplete circle. The anchor 722 and/or the connection point 726 can form an open perimeter or other open shapes. The open shape may facilitate removal of the anchor 722 from the surrounding tissue, cartilage, or bone. In some embodiments, the elongate body 702 can be integrally formed. The anchor 722, the strut 712, and the connection point 726 can form a continuous structure.

FIG. 9 illustrates an elongate body 802 of a cartilage support implant 800. The cartilage support implant 800 can include a plurality of elongate bodies, as described herein. FIG. 9 illustrates a nasal valve implant concept. The implant can include an elongate body laser cut from plastic or metal sheet. The implant can be molded. The implant can include anchor features. The implant can include variable widths for anchoring. The elongate body 802 can include a first end 806. In some embodiments, the first end 806 is configured to be placed near the nasal bone. The first end 806 can include one or more anchors or anchor features, as describe herein. The elongate body 802 can include a middle portion 808. In some embodiments, the middle portion 808 configured to be placed near the upper lateral cartilage. The elongate body 802 can include a second end 810. In some embodiments, the second end 810 is configured to be placed near the lower lateral cartilage. The second end 810 can include a connection point 826.

The elongate body 802 can include a strut 812. The strut 812 can include an anchor 822. The anchor 822 can be a bifurcated anchor. The anchor 822 can include one or more barbs. In FIG. 9, the anchor 822 includes two barbs but other configurations are contemplated (e.g., one barb, two barbs, three barbs, four barb, five barbs, six barbs, etc.). The barbs can extend outward from a central axis of the elongate body 802. The barbs can be designed to engage tissue, bone, or cartilage. In some embodiments, the barbs curve from the first end 806 toward the second end 810.

The elongate body 802 can include one or more middle extensions. The elongate body 802 can include a first middle extension 862 and a second middle extension 864. The middle extensions 862, 864 can be designed to engage tissue along the length of the elongate body 802. The extensions 862, 864 can be designed to engage the upper lateral cartilage. The extensions 862, 864 can be disposed in the middle portion 808 of the elongate body 802. The extensions 862, 864 can increase a dimension of the elongate body 802. The extensions 862, 864 can increase a width or thickness of the elongate body 802. In some embodiments, the extensions 862, 864 can be fixed in position. The extensions 862, 864 can be flexible or rigid. The extensions 862, 864 can improve anchoring of the elongate body 802. The extensions 862, 864 can be located in the middle portion 808 of the elongate body 802.

In some embodiments, the extensions 862, 864 can be expandable. The elongate body 802 can include a longitudinal axis. The extensions 862, 864 can expand outward from the longitudinal axis. The extensions 862, 864 can expand laterally. The extensions 862, 864 can expand in opposite directions. The extensions 862, 864 can be mirror image of each other. In some embodiments, the extensions 862, 864 can expand from the same location along the length of the elongate body 802. In some embodiments, the extensions 862, 864 can expand from different locations along the length of the elongate body 802. There can also be an aperture between extensions 862, 864 as shown.

FIG. 10 illustrates an elongate body 902 of a cartilage support implant 900. The cartilage support implant 900 can include a plurality of elongate bodies, as described herein. FIG. 10 illustrates a nasal valve implant concept. The implant can include an anchor. The implant can include two anchors which are offset from each other. The implant can include ePTFE or polyester for tissue ingrowth for long term stability. The anchor can be formed of NiTi or super-elastic wire. The anchor can be laser cut. The anchor can be plastic molded. The elongate body 902 can include a first end 906. In some embodiments, the first end 906 is configured to be placed near the nasal bone. The first end 906 can include one or more anchors, as describe herein. The elongate body 902 can include a middle portion 908. In some embodiments, the middle portion 908 is configured to be placed near the upper lateral cartilage. The elongate body 902 can include a second end 910. In some embodiments, the second end 910 configured to be placed near the lower lateral cartilage.

The elongate body 902 can include a first strut 912 and a second strut 914. The first strut 912 and a second strut 914 can be connected by a distal curve 916 at the second end 910. The first strut 912 and the second strut 914 can extend from the distal curve 916 and be parallel. The first strut 912 and the second strut 914 can extend from the distal curve 916 and be skewed. The first strut 912 and the second strut 914 can be separated along the length of the elongate body 902. The two struts 912, 914 can provide support for the elongate body 902. The two struts 912, 914 can be separated at the first end 906. The two struts 912, 914 can be able to flex toward and away from each other at the first end 906.

The first strut 912 can include a first anchor 922. The second strut 914 can include a second anchor 924. Each strut 912, 914 can include an anchor 922, 924 at the first end 910. The anchors 922, 924 are offset anchors. The anchors 922, 924 extend below the plane containing the struts 912, 914. The anchors 922, 924 extend downward from the struts 912, 914 and curve backward toward the second end 910. The anchors 922, 924 can engage tissue, bone, or cartilage. The shape of the anchors 922, 924 can allow for removal of the elongate body 902.

The struts 912, 914 and/or the anchors 922, 924 can include a shape memory material. In some embodiments, the struts 912, 914 and/or the anchors 922, 924 can comprise NiTi. The elongate body 902 can include a sleeve 918. The sleeve 918 can be designed to surround at least a portion of the elongate body 902. The sleeve 918 can be designed to surround the middle portion 908. The distal curve 916 and the sleeve 918 can form a connection point 926. The distal curve 916 and the sleeve 918 can form an enclosed aperture 928. The sleeve 918 can provide support for the struts 912, 914. The sleeve 918 can reduce the flexibility or degree of motion of the struts 912, 914. The sleeve 918 can include a polymer. The sleeve 918 can include ePTFE, polyester, and/or any plastic or plastic-like material. The sleeve 918 can include a material suitable for tissue ingrowth. The sleeve 918 can include bone graft material. The sleeve 918 can include bone cement. The sleeve 918 can include a matrix including bone growth factors. The sleeve 918 can promote tissue ingrowth for permanent installation of the implant. In some embodiments, the elongate body 902 can be formed as a continuous single wire. The anchors 922, 924, the struts 912, 914, and the distal curve 916 can be integrally formed as a single structure.

FIG. 11 illustrates an elongate body 1002 of a cartilage support implant 1000. The cartilage support implant 1000 can include a plurality of elongate bodies, as described herein. FIG. 11 illustrates a nasal valve implant concept. The implant can include a tether hole. The implant can include prolapsable anchors to allow removal. The elongate body 1002 can include a first end 1006. In some embodiments, the first end 1006 is configured to be placed near the nasal bone. The elongate body 1002 can include a middle portion 1008. In some embodiments, the middle portion 1008 is configured to be placed near the upper lateral cartilage. The elongate body 1002 can include a second end 1010. In some embodiments, the second end 1010 is configured to be placed near the lower lateral cartilage. The elongate body 1002 can include a connection point 1026 including any of the features described herein.

The elongate body 1002 can include one or more middle anchors, such as barbs extending radially outwardly both sides of the device, or only one side in other embodiments. The elongate body 1002 can include a first set of middle anchors 1052 and a second set of middle anchors 1054. The middle anchors 1052, 1054 can be designed to engage tissue along the length of the elongate body 1002. The middle anchors 1052, 1054 can be designed to engage the upper lateral cartilage. The middle anchors 1052, 1054 can be disposed in the middle portion 1008 of the elongate body 1002. The middle anchors 1052, 1054 can include one or more barbs to engage tissue. In some embodiments, the middle anchors 1052, 1054 can be fixed in position. The middle anchors 1052, 1054 can be flexible or rigid. In some embodiments, the middle anchors 1052, 1054 can be expandable. The elongate body 1002 can include a central axis. The middle anchors 1052, 1054 can expand outward from the central axis. The middle anchors 1052, 1054 can expand laterally.

The first set of middle anchors 1052 can expand in an opposite direction as the second set of middle anchors 1054. The first set of middle anchors 1052 can expand in a first direction. The second set of middle anchors 1054 can expand in a second direction, opposite the first direction. The first set of middle anchors 1052 can be disposed near the first end 1006. The first set of middle anchors 1052 can point toward the first end 1006. The second set of middle anchors 1054 can be disposed near the second end 1010. The second set of middle anchors 1054 can point toward the second end 1008. The first set of middle anchors 1052 can be considered unidirectional anchors. The second set of middle anchors 1054 can be considered unidirectional anchors.

In some embodiments, two or more anchors from the first set of middle anchors 1052 can expand from the same location along the length of the elongate body 1002 In some embodiments, two or more anchors from the second set of middle anchors 1054 can expand from the same location along the length of the elongate body 1002. In some embodiments, two or more anchors of the middle anchors 1052, 1054 can expand from different locations along the length of the elongate body 1002. The first set of middle anchors 1052 can be retracted to allow for removal of the elongate body 1002. The second set of middle anchors 1054 can be retracted to allow for removal of the elongate body 1002.

FIG. 12 illustrates an elongate body 1102 of a cartilage support implant 1100. The cartilage support implant 1100 can include a plurality of elongate bodies, as described herein. FIG. 12 illustrates a nasal valve implant concept. The elongate body 1102 can include a first end 1106. In some embodiments, the first end 1106 is configured to be placed near the nasal bone. The elongate body 1102 can include a middle portion 1108. In some embodiments, the middle portion 1108 is configured to be placed near the upper lateral cartilage. The elongate body 1102 can include a second end 1110. In some embodiments, the second end 1110 configured to be placed near the lower lateral cartilage. The elongate body 1102 can include a connection point 1126 as described herein.

The elongate body 1102 can include one or more middle anchors. The elongate body 1102 can include a first middle anchor 1152 and a second middle anchor 1154. The middle anchors 1152, 1154 can be disposed in the middle portion 1108 of the elongate body 1102. The middle anchors 1152, 1154 can include one or more barbs to engage tissue. In some embodiments, the middle anchors 1152, 1154 can be expandable. In some embodiments, the middle anchors 1152, 1154 can be retractable. The first middle anchor 1152 can expand in an opposite direction as the second middle anchor 1154. The first middle anchor 1152 can expand in a first direction. The second middle anchor 1154 can expand in a second direction, opposite the first direction. The anchors 1152, 1154 can increase the width of the cartilage support implant 1100.

FIG. 13 illustrates an elongate body 1202 of a cartilage support implant 1200. The cartilage support implant 1200 can include a plurality of elongate bodies, as described herein. FIG. 13 illustrates a nasal valve implant concept. The implant can include no more than a single distal tine, or two or more tines in other embodiments. The implant can include a tether loop. The implant can include a mesh or solid coating. The implant can include an anchor. The elongate body 1202 can include a first end 1206. In some embodiments, the first end 1206 is configured to be placed near the nasal bone. The first end 1206 can include one or more anchors, as describe herein. The elongate body 1202 can include a middle portion 1208. In some embodiments, the middle portion 1208 is configured to be placed near the upper lateral cartilage. The elongate body 1202 can include a second end 1210. In some embodiments, the second end 1210 is configured to be placed near the lower lateral cartilage.

The elongate body 1202 can include a strut 1212. The strut 1212 can provide support for the elongate body 1202. The strut 1212 can include a distal curve 1216. The distal curve 1216 can curve from the second end 1210 toward the first end 1206. The strut 1212 can have a central longitudinal axis. The strut 1212 can include an anchor 1222. The anchor 1222 can be a centered anchor.

The anchor 1222 can be centered along a longitudinal axis of the strut 1212. The anchor 1222 can be centered relative to the longitudinal axis of the strut 1212. In some embodiments, the anchor 1222 lies equally above and below the longitudinal axis. In some embodiments, the longitudinal axis of the strut 1212 extends through a midpoint of the anchor 1222. The anchor 1222 can form a complete or nearly complete circle. The anchor 1222 can form an incomplete circle. The anchor 1222 can form an open perimeter or other open shapes. The open shape may facilitate removal of the anchor 1222 from the surrounding tissue, cartilage, or bone.

The elongate body 1202 can include a connection point 1226. The connection point 1226 can include an aperture 1228 designed to accept a tether. The connection point 1226 can be at the opposite end of the elongate body 1202 as the anchor 1222. The connection point 1226 can extend counterclockwise from the strut 1212. The anchor 1222 can extend clockwise from the strut 1212. The connection point 1226 and the anchor 1222 can extend in opposite direction. The connection point 1226 can form an enclosed perimeter or other closed shape. The closed shape may facilitate retention of the tether within the connection point 1226.

The strut 1212 and/or the anchors 1222 can include a shape memory material. In some embodiments, the strut 1212 and/or the anchors 1222 can comprise NiTi. The elongate body 1202 can include a sleeve 1218. The sleeve 1218 can be designed to surround at least a portion of the elongate body 1202. The sleeve 1218 can be designed to surround the middle portion 1208.

The distal curve 1216 and the sleeve 1218 can form the connection point 1226. The distal curve 1216 and the sleeve 1218 can form an enclosed space. The sleeve 1218 can form a connection between two segments of the distal curve 1216 and/or the strut 1212. The sleeve 1218 can provide support for the strut 1212. The sleeve 1218 can include a mesh. The sleeve 1218 can include a solid coating. The sleeve 1218 can promote tissue ingrowth. In some embodiments, the elongate body 1202 can be formed as a continuous structure. The anchor 1222, the strut 1212, and the distal curve 1216 can be formed from the same material.

Figure 14A:
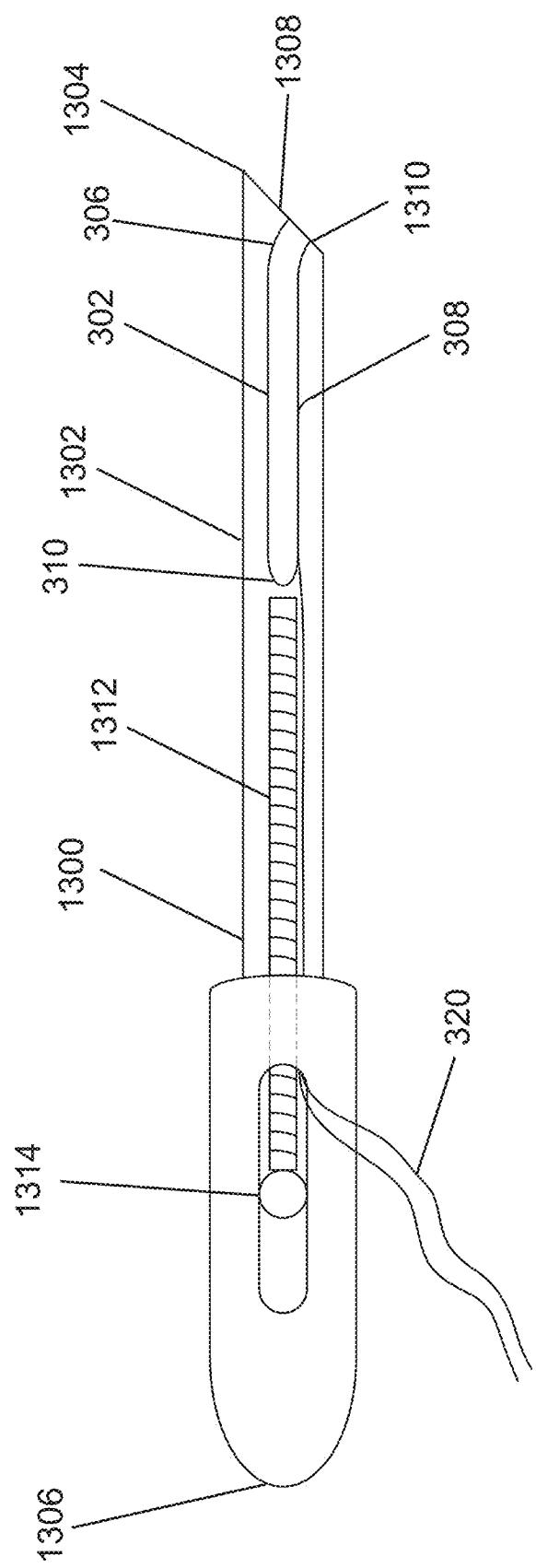

FIGS. 14A-14C illustrate an embodiment of a cartilage support delivery system 1300 for a cartilage support implant. The cartilage support delivery system 1300 can be designed to delivery any cartilage support implant described herein. In some embodiments, the cartilage support delivery system 1300 delivers one elongate body at a time. In some embodiments, the cartilage support delivery system 1300 delivers two or more elongate body simultaneously.

FIGS. 14A-14C illustrate a delivery system for the nasal valve implant. The delivery system 1300 can include a cannula 1302. The cannula 1302 can be hollow. The cannula 1302 can be designed to accept a cartilage support implant therein. The cartilage support implant can be flattened or compressed to fit within the cannula 1302. In some embodiments, one or more anchors are compressed. In some embodiments, one or more middle anchors are compressed. In some embodiments, one or more extensions are compressed. The cartilage support implant can have a low-profile delivery configuration. The cannula 1302 can include a distal end 1304 and a proximal end 1306. The distal end 1304 can be open to allow for delivery of the cartilage support implant. The distal end can include a needle tip 1308.

The proximal end 1306 can be held by a user. The proximal end 1306 can include any feature to increase grip or usability of the delivery system 1300. The delivery system 1300 can include a push rod 1312. The push rod 1312 can be designed to be disposed within the cannula 1302. The push rod 1312 can translate within the cannula 1302 to push the cartilage support implant from the distal end 1304 of the delivery system 1300. The delivery system 1300 can include a deployment knob 1314. The deployment knob 1314 can be designed to translate the push rod 1312 within the cannula 1302.

FIGS. 14A-14C shows the cartilage support implant 300. The delivery system 1300 can be designed to deliver the first elongate body 302, followed by the second elongate body 304. The first elongate 302 can be disposed within the delivery system 1300 for delivery. The first elongate 302 can include the first end 306, the middle portion 308, ant the second end 310. The first elongate 302 can be disposed within the delivery system 1300 such that the first end 306 is closer to the distal end 1304 of the delivery system 1300. The cartilage support implant 300 can be coupled to a tether 320. The tether 320 can be coupled to a connection point as describe herein. In some embodiments, the tether 320 is coupled to the second end 310. In some embodiments, the tether 320 is coupled to the middle portion 308. In some embodiments, the tether 320 is coupled to the first end 306. In some embodiments, the tether 320 is coupled directly to the struts 312, 314 of the first elongate body 302.

The needle tip 1308 can puncture the anatomical features, such as bone, tissue, or cartilage. The needle tip 1308 can be tapered to have a shorter end 1310. The user can position the distal end 1304 within the nasal valve of the patient. The user can position the distal end 1304 near the nasal bone. The distal end 1304 can include one or more radiopaque markers to enhance visibility and facilitate placement of the distal end 1304. The distal end 1304 can be advanced to the position where the first end 306 of the cartilage support implant 300 is to be placed. The distal end 1304 can be advanced to the position where the anchors 322, 324 are to be placed. The needle tip 1308 can be rotated to direct the anchors 322, 324. The anchors 322, 344 can be designed to deploy from the shorter end 1310 of the cannula 1302.

To deploy, the deployment knob 1314 can be first advanced to expose the anchor portion of the implant. The one or more anchors align with the short end 1310 of the needle tip 1308. To deploy the cartilage support implant 300, the deployment knob 1314 can be first advanced to expose the anchor 322, 324. In some embodiments, the deployment knob 1314 can advance the first end 306 from the distal end 1304 of the delivery system 1300. The first end 306 may or may not include an anchor. The deployment knob 1314 can be advanced distally (e.g., from a proximal position to a distal position). In some embodiments, the deployment knob 1314 can be rotated to translate the push rod 1312. Other configurations are contemplated. The push rod 1312 can be advanced distally within the cannula 1302. The one or more anchors 322, 324 are exposed from the distal end 1304. The middle portion 308 and the second end 310 of the cartilage support implant 300 can remain within the cannula 1302. The anchors 322, 324 can expand as described herein. The anchors 322, 324 can curve to a pre-determined shape. The anchors 322, 324 can engage tissue, bone, or cartilage as the anchors 322, 324 are expanded.

The delivery system 1300 can be retracted. The delivery system 1300 can slide over the middle portion 308 and the second end 310. The cartilage support implant 300 can be pulled out of the cannula 1302. The tether 320 can remain attached to the cartilage support implant 300. The tether 320 can allow for the removal or repositioning of the cartilage support implant 300. To reposition, the cannula 1302 can slides over the second end 310 and middle portion 308. In some methods of use, as the cannula 1032 slides along the cartilage support implant 300, the cannula 1302 can cause the anchors 322, 324 to straighten. In some methods of use, the elongate body 302 of the cartilage support implant 300 can be pulled by the tether 320. The anchors 322, 344 are pulled into the cannula 1302 by the tether 320. Other configurations for retraction are contemplated.

Figure 15A:
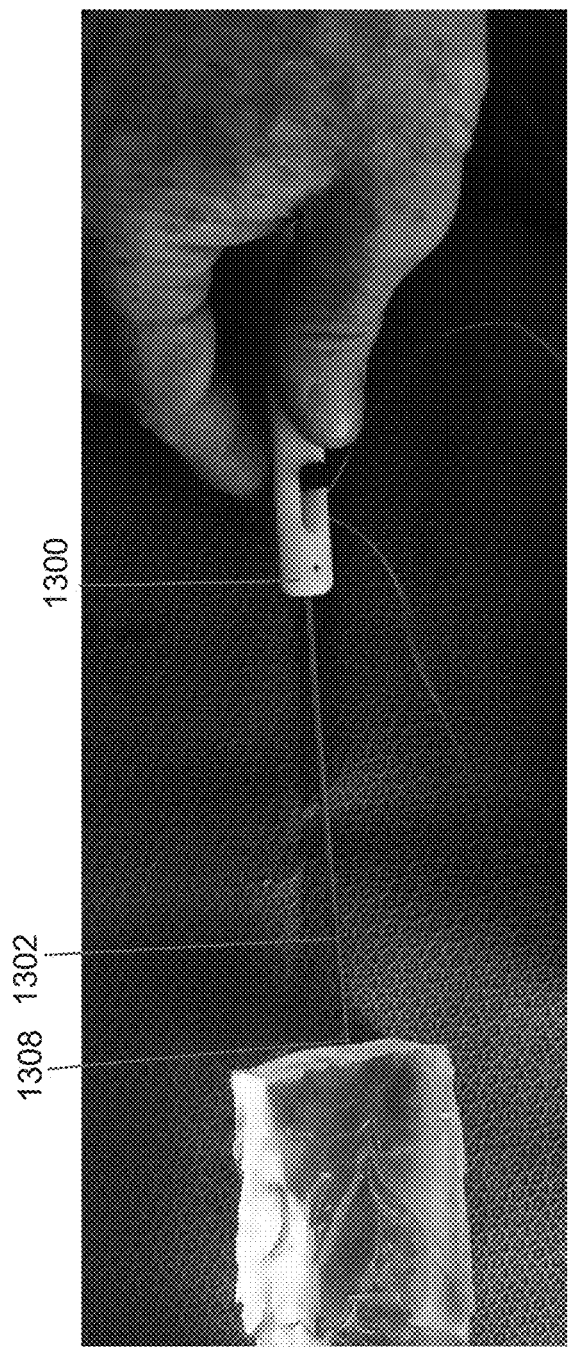

FIGS. 15A-15L illustrate methods of use of the cartilage support implant 300 and the cartilage support delivery system 1300. FIG. 15A illustrates the delivery system 1300 approaching the patient. The elongate body 302 of the cartilage support implant 300 can be compressed within the cannula 1302. The distal end 1304 approaches the anatomy of the patient. In the illustrated example, a clear block is utilized schematically as representative of the anatomy of a patient.

Figure 15B:
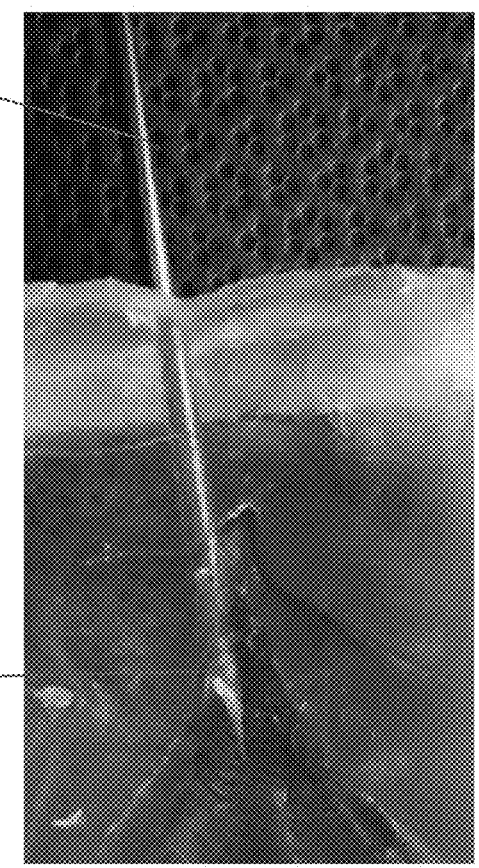

FIG. 15B illustrates the needle tip 1308 of the delivery system 1300 penetrating the patient. The elongate body 302 of the cartilage support implant 300 can be compressed within the cannula 1302. The needle tip 1308 can puncture through tissue, cartilage, and/or bone. The needle tip 1308 can form a straight path.

FIG. 15C illustrates the first end 306 of the elongate body 302 extending from the cannula 1302 of the delivery system 1300. The delivery system 1300 can include the push rod 1312. The push rod 1312 can apply a force such that the first end 306 of the elongate body 302 extends from the short end 1310 of the needle tip 1308. The first end 306 of the elongate body 302 can include the first anchor 322 and the second anchor 324. The first anchor 322 and the second anchor 324 can extend from the cannula 1302. As the first anchor 322 and the second anchor 324 expands, the first anchor 322 and the second anchor 324 can assume a pre-formed curved shape. The first anchor 322 and the second anchor 324 can include a shape memory material. The first anchor 322 and the second anchor 324 can curve outward. FIG. 15C illustrates the beginning of the curve for the first anchor 322 and the second anchor 324.

FIG. 15D illustrates the first anchor 322 and the second anchor 324 deployed. The push rod 1312 can continue to apply a force until the first anchor 322 and the second anchor 324 are fully extended from the cannula 1302. The first anchor 322 and the second anchor 324 can assume a pre-formed curved shape. The first anchor 322 and the second anchor 324 can curve back toward the proximal end of the cannula 1302. The first anchor 322 and the second anchor 324 can engage tissue, cartilage, or bone. The first anchor 322 and the second anchor 324 can penetrate the surrounding anatomy. The first anchor 322 and the second anchor 324 can become embedded.

FIG. 15E illustrates the cannula 1302 of the delivery system 1300 retracting along the elongate body 302. The elongate body 302 of the cartilage support implant 300 can be released from within the cannula 1302.

FIG. 15F illustrates the cannula 1302 of the delivery system 1300 as the cannula 1302 is removed from the body of the patient. The elongate body 302 of the cartilage support implant 300 can be completely released from within the cannula 1302. The struts 312, 314 can be exposed. In some embodiments, one or more extensions or middle anchors are deployed or expanded as the cannula 1302 of the delivery system 1300 retracts. The connection point 326 can be released from the cannula 1302. In some embodiments, the connection point 326 is deployed or expanded as the cannula 302 of the delivery system 1300 retracts. The connection point 326 can be coupled with the tether 320. The connection point 326 can be designed to be retained within the patient, for instance near the lower lateral cartilage. The tether 320 can extend from the lower lateral cartilage and out of the nose of the patient.

Figure 15G:
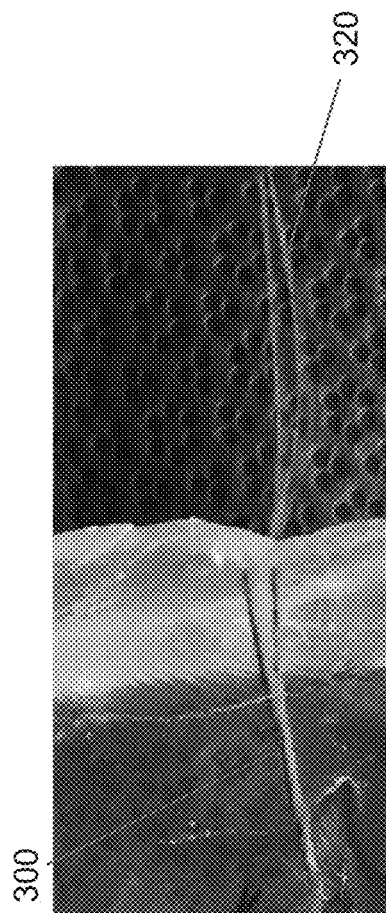

FIG. 15G illustrates the delivery system 1300 completed removed. The tether 320 extends from the connection point 326. In some methods of use, the tether 320 is removed. In some methods of use, the tether 320 can be removed once the position of the elongate body 302 of the cartilage support implant 300 is verified such as through imaging. The elongate body 302 of the cartilage support implant 300 can include a non-resorbable material such as a metal which can be radiopaque. The elongate body 302 of the cartilage support implant 300 can be designed to be a stabilizing stent for the nasal valve. The elongate body 302 of the cartilage support implant 300 can be a permanent implant. The process can be repeated to deploy one or more additional elongate bodies. The elongate bodies can be placed in a parallel arrangement along the midline of a patient's nose. In some methods of use, two elongate bodies are deployed. Each elongate body can extend from the nasal bone to the lower lateral cartilage.

Figure 15H:
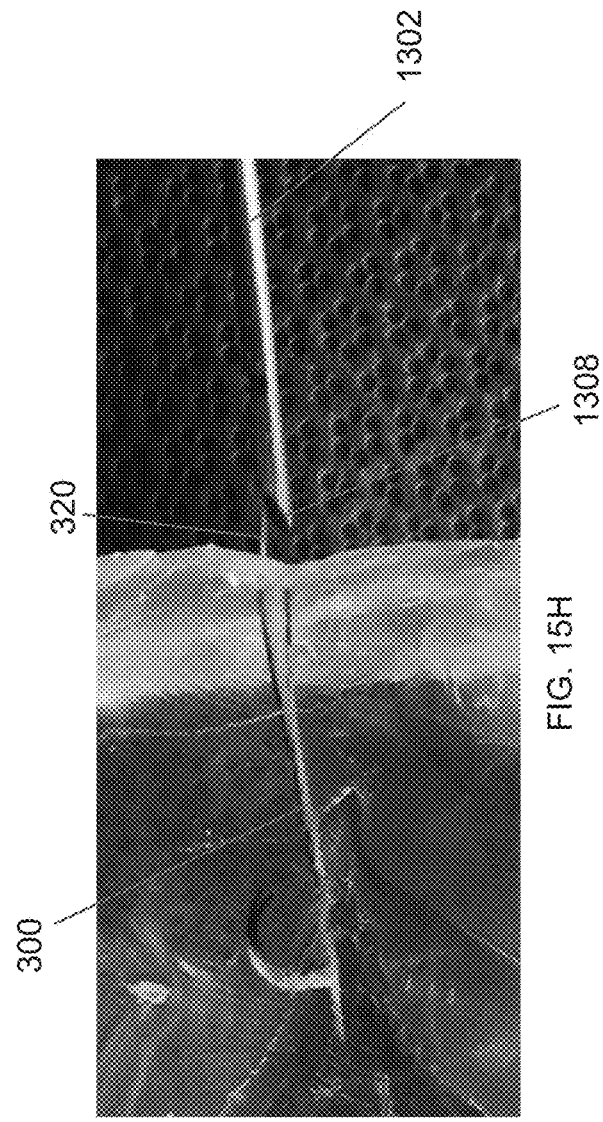

FIG. 15H illustrates the needle tip 1308 of the delivery system 1300 sliding along the tether 320. In some methods of use, the elongate body 302 of the cartilage support implant 300 can be retrieved. In some methods of use, the elongate body 302 of the cartilage support implant 300 can be repositioned.

Figure 15I:
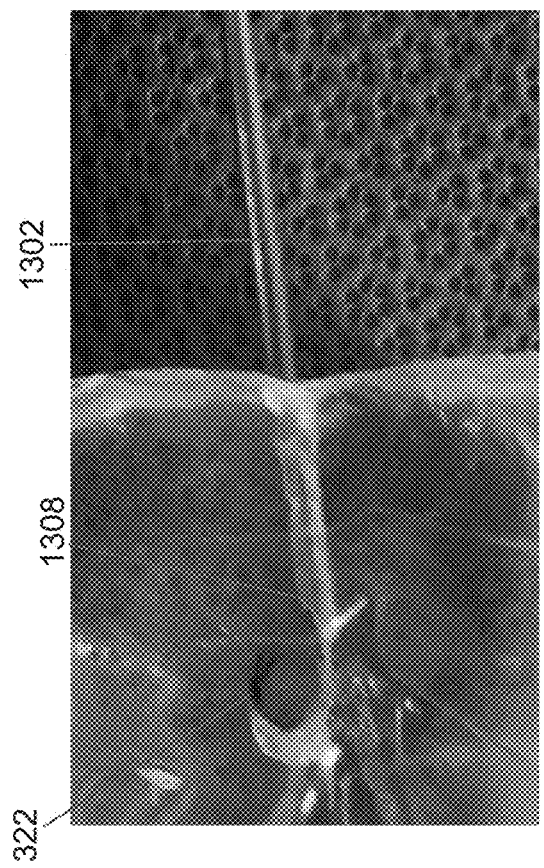

FIG. 15I illustrates the needle tip 1308 of the delivery system 1300 penetrating the patient again. The needle tip 1308 of the delivery system 1300 can penetrate the patient. The elongate body 302 of the cartilage support implant 300 can be compressed by the cannula 1302. The cannula 1302 can slide along the struts 312, 324 of the elongate body 302. The struts 312, 314 can be compressed. In some embodiments, one or more extensions or middle anchors are compressed as the cannula 1302 of the delivery system 1300 advances. The needle tip 1308 of the delivery system 1300 advances along the struts 312, 314 and toward the anchors 322, 324. In some methods of use, the elongate body 302 of the cartilage support implant 300 can be retrieved after a period of time (e.g., one day, one month, one year, many years, etc.). In some methods of use, the elongate body 302 of the cartilage support implant 300 can be retrieved during the same procedure as deployment (e.g., time period of one minute, ten minutes, twenty minutes, one hour, etc.). In some embodiments, the device is not placed adjacent to the maxillary bone.

Figure 15J:
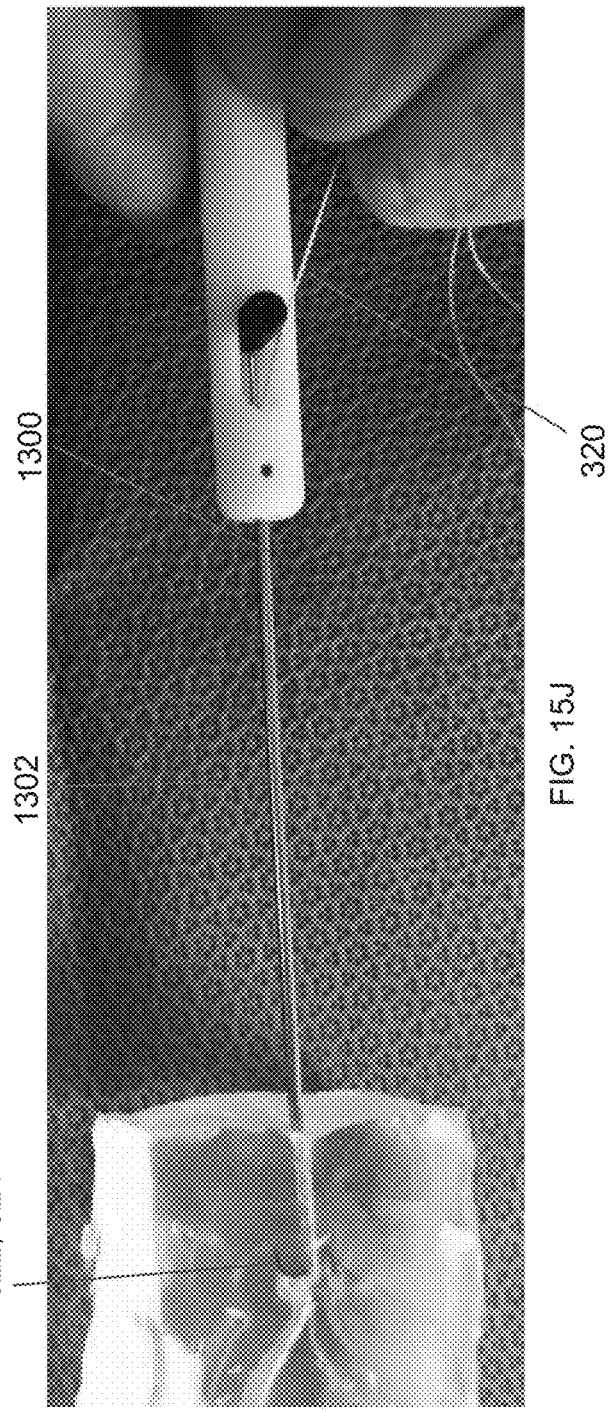

FIG. 15J illustrates the tension applied to the tether 320. The tether 320 can extend from the connection point 326. In some methods of use, the tether 320 is pulled to apply tension to the elongate body 302. The tether 320 applies a force to the elongate body 302. The needle tip 1308 of the delivery system 1300 can be near the end of the struts 312, 314 when tension is applied. The needle tip 1308 of the delivery system 1300 can be near the anchors 322, 324 when tension is applied.

Figure 15K:
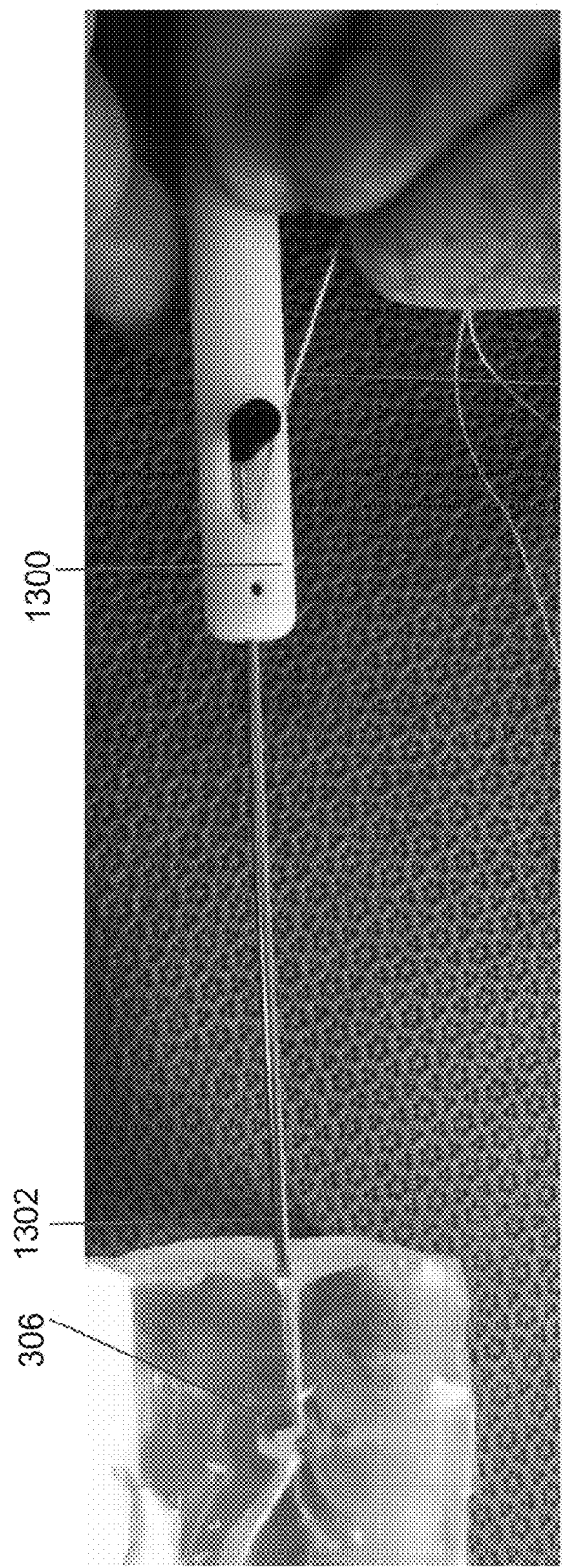

FIG. 15K illustrates the first end 306 of the elongate body 302 retracting into the cannula 1302 of the delivery system 1300. The tether 320 can apply a force such that the first end 306 of the elongate body 302 retracts along the deployment curve of the first end 306 of the elongate body 302. The first end 306 of the elongate body 302 can include the first anchor 322 and the second anchor 324. The first anchor 322 and the second anchor 324 can retract into the cannula 1302. As the first anchor 322 and the second anchor 324 retracts, the first anchor 322 and the second anchor 324 can follow a curved shape toward the cannula 1302.

Figure 15L:
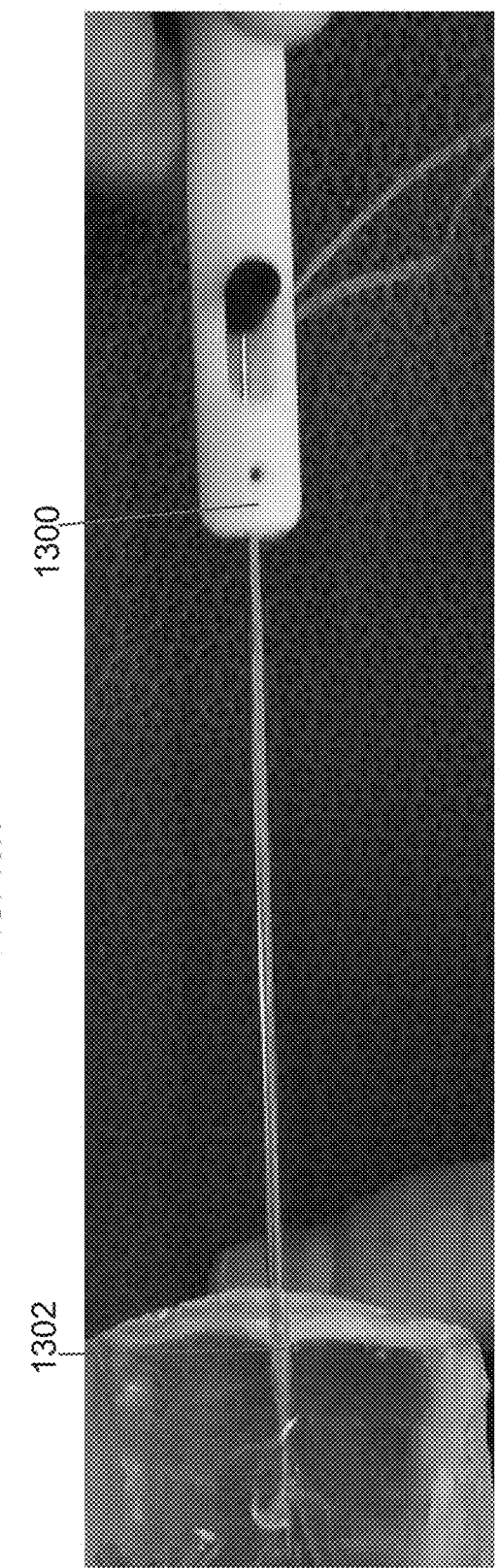

FIG. 15L illustrates the cannula 1302 of the delivery system 1300 as the cannula 1302 is removed from the body of the patient. The elongate body 302 of the cartilage support implant 300 can be compressed within the cannula 1302.

Figure 16D:
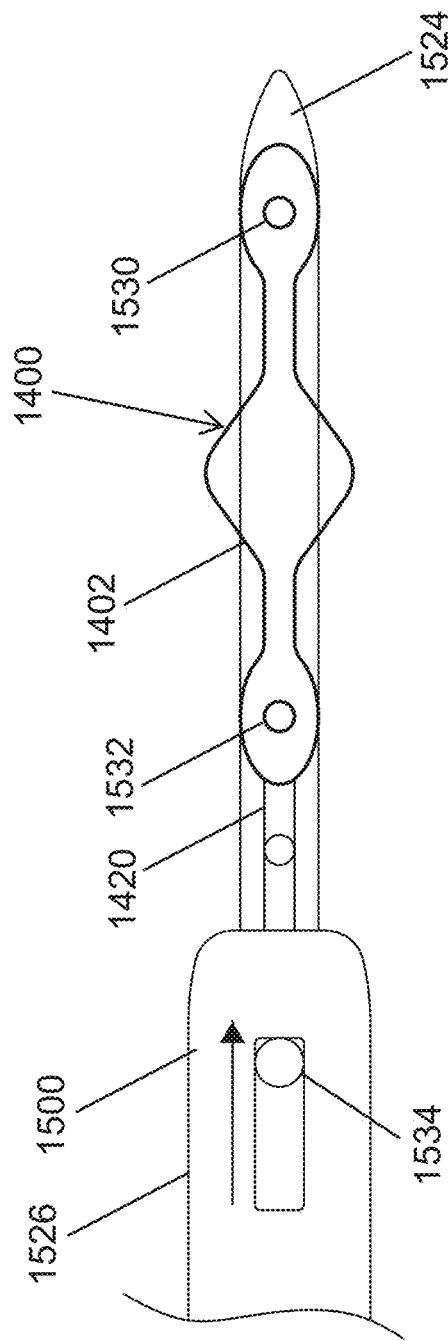

FIGS. 16A-16I illustrate an embodiment of a cartilage support implant 1400 and a cartilage support delivery system 1500. FIG. 16A illustrates an elongate body 1402 of a cartilage support implant 1400. The cartilage support implant 1400 can include a plurality of elongate bodies, as described herein. The implant can include two or more expandable sections. The implant can be about 0.6" in length. Other lengths are contemplated (e.g., about 0.1", 0.2" 0.3", 0.4", 0.5", 0.65", 0.7", 0.8", 0.9", 1.", etc. or ranges incorporating two of the aforementioned values). The elongate body 1402 can include a first end 1406. In some embodiments, the first end 1406 configured to be placed near the nasal bone. The first end 1406 can include one or more anchors, as describe herein. The elongate body 1402 can include a middle portion 1408. In some embodiments, the middle portion 1406 is configured to be placed near the upper lateral cartilage. The elongate body 1402 can include a second end 1410. In some embodiments, the second end 1410 is configured to be placed near the lower lateral cartilage. The cartilage support implant 1400 can include any feature of the cartilage support implants described herein.

The elongate body 1402 can include a first strut 1412 and a second strut 1414. The first strut 1412 and a second strut 1414 can be connected by a distal curve 1416 at the second end 1410. The first strut 1412 and the second strut 1414 can extend from the distal curve 1416 and be parallel for at least a portion of the length. The distal curve 1416 can form the connection point 1426. The first strut 1412 and the second strut 1414 can be separated along the length of the elongate body 1402. The two struts 1412, 1414 can be connected by a proximal curve 1430. The proximal curve 1416 can form the anchor 1422. The proximal curve 1416 can form the first end 1406.

The anchor 1422 and/or the connection point 1426 can form a complete or nearly complete circle. The anchor 1422 and/or the connection point 1426 can form an enclosed perimeter or other closed shape. The closed shape may facilitate retention of the tether within the connection point 1426. The anchor 1422 and/or the connection point 1426 can be fixed in position or expandable.

The elongate body 1402 can include one or more middle extensions. The elongate body 1402 can include a first middle extension 1462 and a second middle extension 1464. The middle extensions 1462, 1464 can be designed to engage tissue along the length of the elongate body 1402. The extensions 1462, 1464 can be designed to engage the upper lateral cartilage. The extensions 1462, 1464 can be disposed in the middle portion 1408 of the elongate body 1402. The extensions 1462, 1464 can increase a dimension of the elongate body 1402. The extensions 1462, 1464 can increase a width or thickness of the elongate body 1402. The extensions 1462, 1464 can be fixed in position or expandable.

FIGS. 16B-16C illustrate an embodiment of a cartilage support delivery system 1500 for a cartilage support implant. The cartilage support delivery system 1500 can be designed to delivery any cartilage support implant described herein. In some embodiments, the cartilage support delivery system 1500 delivers one elongate body at a time. In some embodiments, the cartilage support delivery system 1500 delivers two or more elongate body simultaneously.

The delivery system 1500 can include an inserter 1522. The inserter 1522 can be solid, such as a solid needle. The inserter 1522 can be designed to accept a cartilage support implant thereon. The cartilage support implant can be flattened or compressed to fit onto the inserter 1522 as described herein. In some embodiments, one or more anchors are compressed. In some embodiments, one or more middle anchors are compressed. In some embodiments, one or more extensions are compressed. In some embodiments, one or more connection points are compressed. The cartilage support implant can have a low-profile delivery configuration. The inserter 1522 can include a distal end 1524 and a proximal end 1526. The distal end 1524 can be open or closed. The distal end 1524 can include a needle tip 1528.

The proximal end 1526 can be held by a user. The proximal end 1526 can include a handle. The proximal end 1526 can include any feature to increase grip or usability of the delivery system 1500. The delivery system 1500 can include a first hook 1530 and a second hook 1532. The first hook 1530 can be distal to the second hook 1532. The first hook 1530 can be designed to be disposed on or coupled to the inserter 1522. The first hook 1530 can be fixed. The second hook 1532 can be designed to be disposed on or coupled to the inserter 1522. The second hook 1532 can be movable. The second hook 1532 can translate relative to the inserter 1522 to compress the cartilage support implant such as the elongate body 1402 of the cartilage support implant 1400. The second hook 1532 can translate proximally toward the proximal end 1526 to compress the implant. The delivery system 1500 can include a deployment knob 1534. The deployment knob 1534 can be designed to translate the second hook 1332 relative to the inserter 1522. FIGS. 16B-16C illustrate the delivery system 1500 including the delivery inserter, the first hook and the second hook. The implant is held via tension between the two hooks. The implant is applied with sliding knob attached to the proximal hook.

Figure 16E:
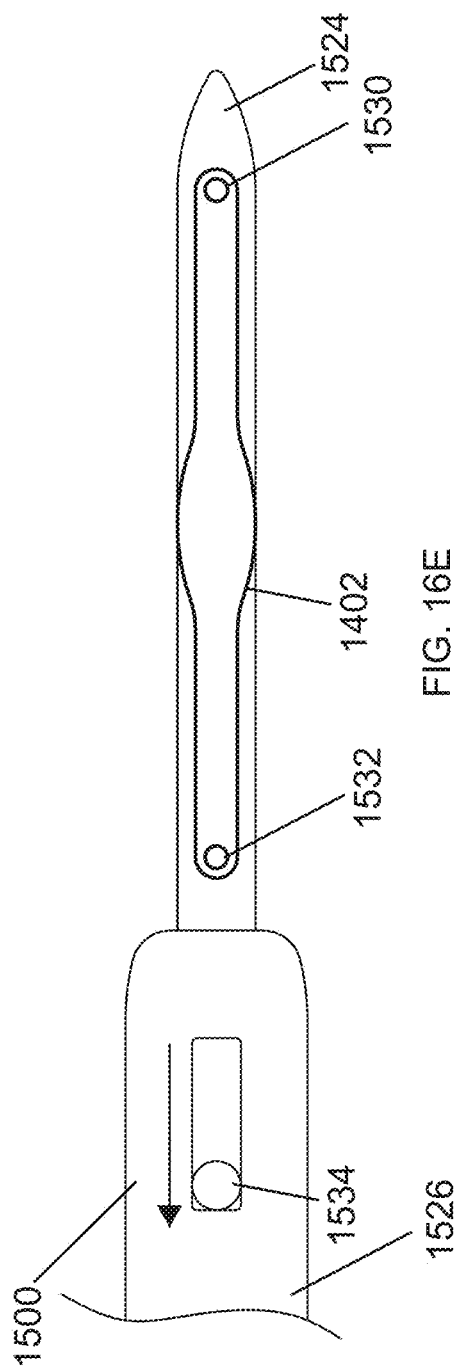

FIGS. 16D-16E illustrates the elongate body 1402 of the cartilage support implant 1400 and the delivery system 1500. The delivery system 1500 can be designed to deliver the first elongate 1402, followed by a second elongate body (not shown). The first elongate 1402 can be disposed onto the delivery system 1500 for delivery. The cartilage support implant 1400 can be coupled to a tether 1420. The tether 1420 can be coupled to the connection point 1426 as describe herein. In some embodiments, the tether 1420 is coupled to the second end 1410. In some embodiments, the tether 1420 is coupled directly to the first strut 1412 and/or the second strut 1414 of the first elongate body 1402.

To compress the elongate body 1402, the anchor 1422 is coupled to the first hook 1530. The anchor 1422 can form an enclosed shaped designed to fit around the first hook 1530. The connection point 1426 is coupled to the second hook 1532. The deployment knob 1534 can be coupled to the second hook 1532. FIG. 15D illustrates the elongate body 1402 loaded onto the first hook 1530 and the second hook 1532. The first hook 1530 and the second hook 1532 hold the elongate body 1402 in the expanded configuration. The deployment knob 1534 can slide to apply tension to the elongate body 1402. FIG. 15E illustrates the elongate body 1402 with tension applied by the first hook 1530 and the second hook 1532. The implant deforms to low profile with tension. FIG. 15D illustrates the un-tensioned state. FIG. 16E illustrates the tensioned state. The system can include a handle at the proximal end 1526. The handle can facilitate grip of the delivery system while tension is being applied. The system can include the implant, such as any implant described herein. The distal end can include a trocar or inserter shaft. The system can include retainer hooks.

FIGS. 16F-16H illustrates end views of the inserter shaft. FIG. 16F shows the implant, the retainer and the shaft. The implant can be any cartilage support implant described herein, including cartilage support implant 1400. The retainer can be the first hook 1530 or the second hook 1532. The shaft can be a portion of the inserter 1522 along the length. In FIG. 16F, the shaft of the inserter 1522 is cup-shaped or concave. The concave shape may facilitate retention of the implant. The retainer is T-shaped. Other shapes for the first hook 1530 and the second hook 1532 are contemplated (e.g., J-shaped, S-shaped, U shaped, etc.). In FIG. 16G, the shaft of the inserter 1522 is block-shaped. The sides of the inserter 1522 can be rounded. The implant can be retained on a flat surface. In FIG. 16H, the shaft of the inserter 1522 is cannulated, hollow or ring-shaped. The sides of the inserter 1522 can be rounded. The implant can be retained on a rounded surface.

Figure 16I:
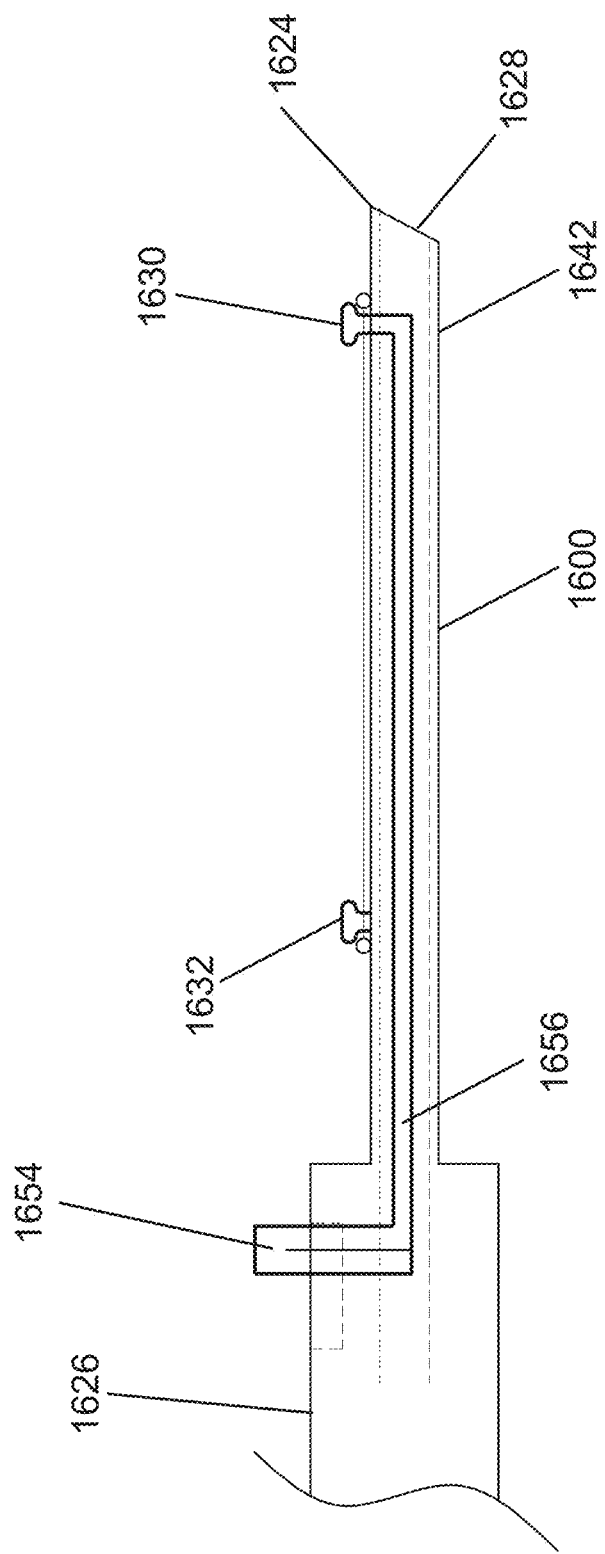

FIG. 16I illustrates another embodiment of a delivery system 1600. The cartilage support delivery system 1600 can be designed to delivery any cartilage support implant described herein. In some embodiments, the cartilage support delivery system 1600 delivers one elongate body at a time. In some embodiments, the cartilage support delivery system 1600 delivers two or more elongate body simultaneously.

The delivery system 1600 can include an inserter 1642. The inserter 1642 can be a hypotube or other cannulated structure. The inserter 1642 can be designed to accept a cartilage support implant thereon. The cartilage support implant can be flattened or compressed to fit onto the inserter 1642 as described herein. The inserter 1642 can include a distal end 1624 and a proximal end 1626. The distal end 1624 can include a needle tip 1628.

The proximal end 1626 can be held by a user. The delivery system 1600 can include a first hook 1630 and a second hook 1632. The first hook 1630 can be distal to the second hook 1632. The first hook 1630 can be designed to be disposed on or coupled to the inserter 1622. The first hook 1630 can be movable. The second hook 1632 can be designed to be disposed on or coupled to the inserter 1622. The second hook 1632 can be fixed.

The first hook 1630 can translate relative to the inserter 1642 to compress the cartilage support implant such as the elongate body 1402 of the cartilage support implant 1400. The first hook 1630 can translate distally toward the distal end 1624 to compress the implant. The delivery system 1600 can include a deployment knob 1654. The deployment knob 1654 can be designed to translate the first hook 1630 relative to the inserter 1622. The deployment knob 1654 can be coupled to a pushrod 1656. The pushrod 1656 can translated within the cannula of the inserter 1642. The pushrod 1656 can be coupled to both the deployment knob 1654 and the first hook 1630. Upon movement of the deployment knob 1654, the first hook 1630 can translate to apply tension to the implant. Other configurations are contemplated.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:
1. A cartilage support implant comprising:
a first elongate body configured to reside within a nose of a patient, the first elongate body comprising a first end and a second end, opposite the first end,
wherein anchors of the first elongate body consist of a first anchor and a second anchor located in between the first end and the second end along a central portion of the first elongate body, the first anchor configured to have a first anchor compressed shape and a first anchor expanded shape, wherein the first anchor expanded shape comprises a curved shape extending toward the second end of the first elongate body thereby forming the first anchor, the second anchor configured to have a second anchor compressed shape and a second anchor expanded shape, wherein the second anchor expanded shape comprises a curved shape extending toward the first end of the first elongate body thereby forming the second anchor, the first anchor expanded shape and the second anchor expanded shape configured to anchor the first elongate body, the first anchor and the second anchor curving in opposite directions, wherein the implant is made of bioresorbable material and is configured to provide support to nasal cartilages within the nose.

2. The cartilage support implant according to claim 1, wherein the first anchor curves between 5 and 360 degrees.

3. A cartilage support implant comprising:

a first elongate body configured to reside within a nose of a patient, the first elongate body comprising a first end and a second end, opposite the first end, wherein the first elongate body consists of a first anchor and a second anchor located in between the first end and the second end along a central portion of the first elongate body, the first anchor configured to have a first anchor compressed shape and a first anchor expanded shape, wherein the first anchor expanded shape comprises a curved shape extending toward the second end of the first elongate body thereby forming the first anchor, the second anchor configured to have a second anchor compressed shape and a second anchor expanded shape, wherein the second anchor expanded shape comprises a curved shape extending toward the first end of the first elongate body thereby forming the second anchor, the first anchor expanded shape and the second anchor expanded shape configured to anchor the first elongate body, the first anchor and the second anchor curving in opposite directions, wherein the implant is made of bioresorbable material and is configured to provide support to nasal cartilages within the nose.

4. The cartilage support implant according to claim 1, wherein the first elongate body is configured to be trimmed for length when in the first anchor compressed shape and the second anchor compressed shape.

5. The cartilage support implant according to claim 1, wherein the first elongate body comprises a connection point.

6. The cartilage support implant according to claim 1, wherein the first anchor and the second anchor are on opposite sides of the first elongate body.

7. The cartilage support implant according to claim 1, wherein the first anchor and the second anchor are axially offset along the length of the first elongate body.

8. The cartilage support implant according to claim 1, wherein the first anchor comprises a barb to engage tissue.

9. The cartilage support implant according to claim 1, wherein the cartilage support implant comprises a plurality of elongate bodies.

10. The cartilage support implant according to claim 1, wherein the first anchor is expandable and retractable.

11. The cartilage support implant according to claim 1, wherein the first anchor increases the width of the cartilage support implant.

12. The cartilage support implant according to claim 1, wherein the second end comprises an aperture configured to accept a tether.

13. The cartilage support implant according to claim 1, further comprising a second elongate body configured to reside within the nose of the patient, wherein the second elongate body is made of bioresorbable material and is configured to provide support to nasal cartilages within the nose.

14. The cartilage support implant according to claim 3, wherein the first anchor and the second anchor comprise one or more barbs.

15. The cartilage support implant according to claim 3, wherein the first anchor and the second anchor are retractable.

16. The cartilage support implant according to claim 1, wherein the first elongate body is configured to prevent the collapse of the nasal valve.

17. The cartilage support implant according to claim 1, wherein the first elongate body comprises a coating to promote tissue ingrowth.

18. The cartilage support implant according to claim 3, wherein the first elongate body functions as a stent across the upper lateral cartilage and the lower lateral cartilage and along the nasal bone.

19. The cartilage support implant according to claim 1, wherein the first elongate body comprises a single length of material.

20. The cartilage support implant according to claim 1, wherein the first end and the second end are rounded.

21. The cartilage support implant according to claim 1, wherein the cartilage support implant is configured to resist movement in opposite directions.

22. The cartilage support implant according to claim 3, wherein the first anchor curves between 5 and 360 degrees, wherein the second anchor curves between 5 and 360 degrees.

23. The cartilage support implant according to claim 3, wherein the first elongate body comprises a connection point.

24. The cartilage support implant according to claim 3, wherein the first anchor and the second anchor are on opposite sides of the first elongate body.

25. The cartilage support implant according to claim 3, wherein the first anchor and the second anchor are axially offset along the length of the first elongate body.

* * * * *